United States Patent
Reich et al.

(10) Patent No.: US 11,583,400 B2
(45) Date of Patent: *Feb. 21, 2023

(54) TECHNIQUES FOR GUIDED ADVANCEMENT OF A TOOL

(71) Applicant: Edwards Lifesciences Innovation (Israel) Ltd., Caesarea (IL)

(72) Inventors: Tal Reich, Moledet (IL); Eran Miller, Moshav Beit Elazari (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 345 days.

This patent is subject to a terminal disclaimer.

(21) Appl. No.: 16/796,262

(22) Filed: Feb. 20, 2020

(65) Prior Publication Data
US 2020/0188104 A1 Jun. 18, 2020

Related U.S. Application Data

(60) Continuation of application No. 15/669,003, filed on Aug. 4, 2017, now Pat. No. 10,610,360, which is a
(Continued)

(51) Int. Cl.
*A61F 2/24* (2006.01)
*A61B 17/04* (2006.01)
(Continued)

(52) U.S. Cl.
CPC ........ *A61F 2/2427* (2013.01); *A61B 17/0401* (2013.01); *A61B 17/3209* (2013.01);
(Continued)

(58) Field of Classification Search
CPC .... A61F 2/2457; A61F 2/2466; A61F 2/2445; A61F 2/2487; A61F 2220/0016;
(Continued)

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CN 113331995 A 9/2021
EP 1034753 A1 9/2000
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Katherine M Shi
(74) *Attorney, Agent, or Firm* — Thomas C. Richardson

(57) ABSTRACT

A sheath is transluminally introduced a sheath into an atrium of a heart of a subject. A guide member is advanced out of the sheath and to a chorda tendinea of the heart, the guide member having a proximal portion that includes a longitudinal element, and a distal portion that includes a helical chord-engaging element. The chord-engaging element is wrapped around the chorda tendinea. While the chord-engaging element remains wrapped around the chorda tendinea, (i) the chord-engaging element is slid over the chorda tendinea toward a papillary muscle that is coupled to the chorda tendinea; and (ii) subsequently, a tool is moved out of the sheath and toward the papillary muscle by sliding the tool along the longitudinal element. Other embodiments are also described.

14 Claims, 10 Drawing Sheets

Related U.S. Application Data division of application No. 14/650,114, filed as application No. PCT/IL2013/050992 on Dec. 3, 2013, now Pat. No. 9,730,793.

(60) Provisional application No. 61/733,979, filed on Dec. 6, 2012.

(51) Int. Cl.

| | |
|---|---|
| *A61B 17/3209* | (2006.01) |
| *A61M 25/04* | (2006.01) |
| *A61B 17/00* | (2006.01) |
| *A61B 17/22* | (2006.01) |
| *A61B 17/34* | (2006.01) |
| *A61M 25/09* | (2006.01) |

(52) U.S. Cl.
CPC .......... *A61F 2/2457* (2013.01); *A61F 2/2466* (2013.01); *A61B 2017/00243* (2013.01); *A61B 2017/00247* (2013.01); *A61B 2017/044* (2013.01); *A61B 2017/0409* (2013.01); *A61B 2017/0441* (2013.01); *A61B 2017/0443* (2013.01); *A61B 2017/0464* (2013.01); *A61B 2017/22042* (2013.01); *A61B 2017/22047* (2013.01); *A61B 2017/3488* (2013.01); *A61M 25/04* (2013.01); *A61M 25/09* (2013.01); *A61M 2025/09183* (2013.01)

(58) Field of Classification Search
CPC ............ A61F 2/2451; A61F 2250/0007; A61F 2/2409; A61F 2/2436; A61F 2250/0004; A61F 2/2412; A61F 2/2427; A61F 2/2442; A61B 17/0401; A61B 2017/00243; A61B 2017/0496; A61B 2017/0409; A61B 2017/00783
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |

(56) References Cited

U.S. PATENT DOCUMENTS

| | | |
|---|---|---|
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian |
| 7,364,588 B2 | 4/2008 | Mathis |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |

(56) References Cited

U.S. PATENT DOCUMENTS

| | | |
|---|---|---|
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Garnbale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |

(56) References Cited

U.S. PATENT DOCUMENTS

| | | |
|---|---|---|
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropouios et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049952 A1 | 3/2007 | Weiss |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |

(56) References Cited

U.S. PATENT DOCUMENTS

| | | |
|---|---|---|
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0005863 A1* | 1/2009 | Goetz .................. A61F 2/2439 623/2.18 |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0218620 A1* | 9/2011 | Meiri .................. A61F 2/2409 623/2.11 |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |

(56) References Cited

U.S. PATENT DOCUMENTS

| | | |
|---|---|---|
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0060328 A1 | 3/2013 | Rothstein |
| 2013/0079873 A1 | 3/2013 | Migliazza et al. |
| 2013/0085529 A1 | 4/2013 | Housman |
| 2013/0090724 A1 | 4/2013 | Subramanian |
| 2013/0096673 A1 | 4/2013 | Hill et al. |
| 2013/0116776 A1 | 5/2013 | Gross et al. |
| 2013/0123910 A1 | 5/2013 | Cartledge |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2022/0096232 A1 | 3/2022 | Skaro et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |

(56) References Cited

FOREIGN PATENT DOCUMENTS

| WO | 2021014440 A2 | 1/2021 |
|---|---|---|
| WO | 2021038559 A1 | 3/2021 |
| WO | 2021038560 A1 | 3/2021 |

OTHER PUBLICATIONS

Ahmadi, A., G. Splllner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet, prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

FIG. 9
FIG. 10
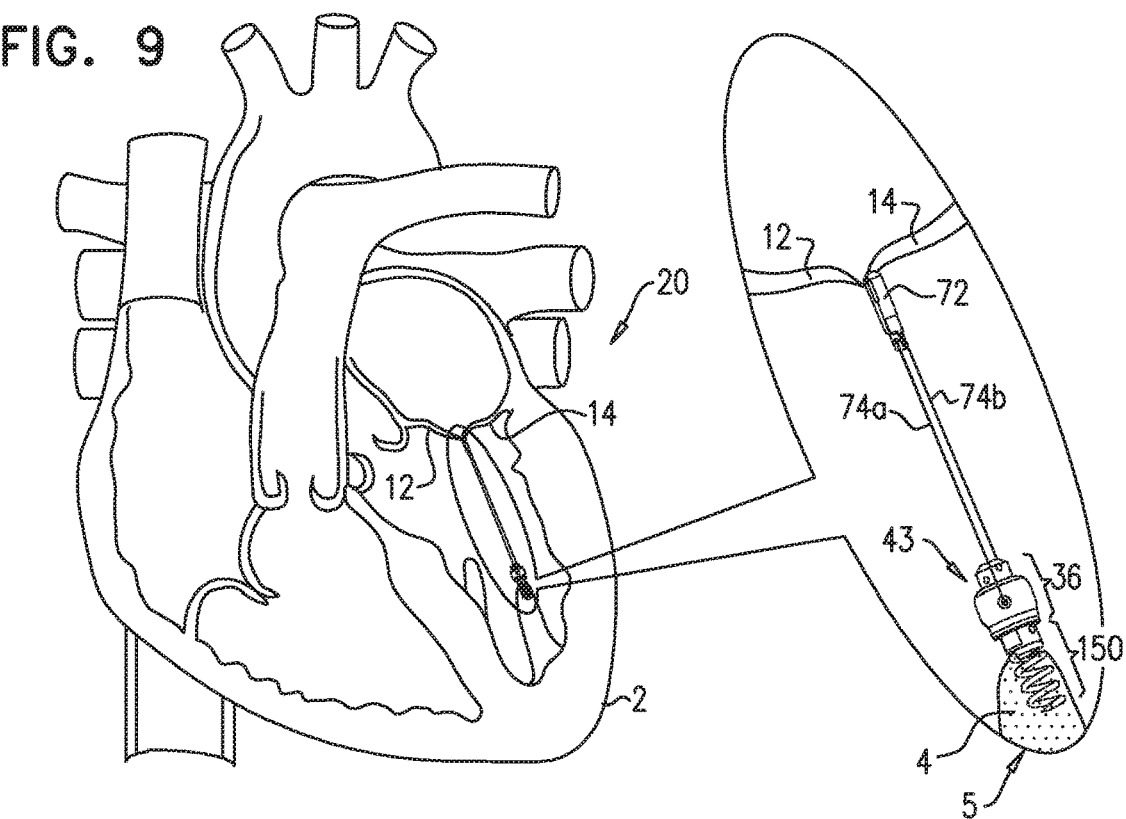
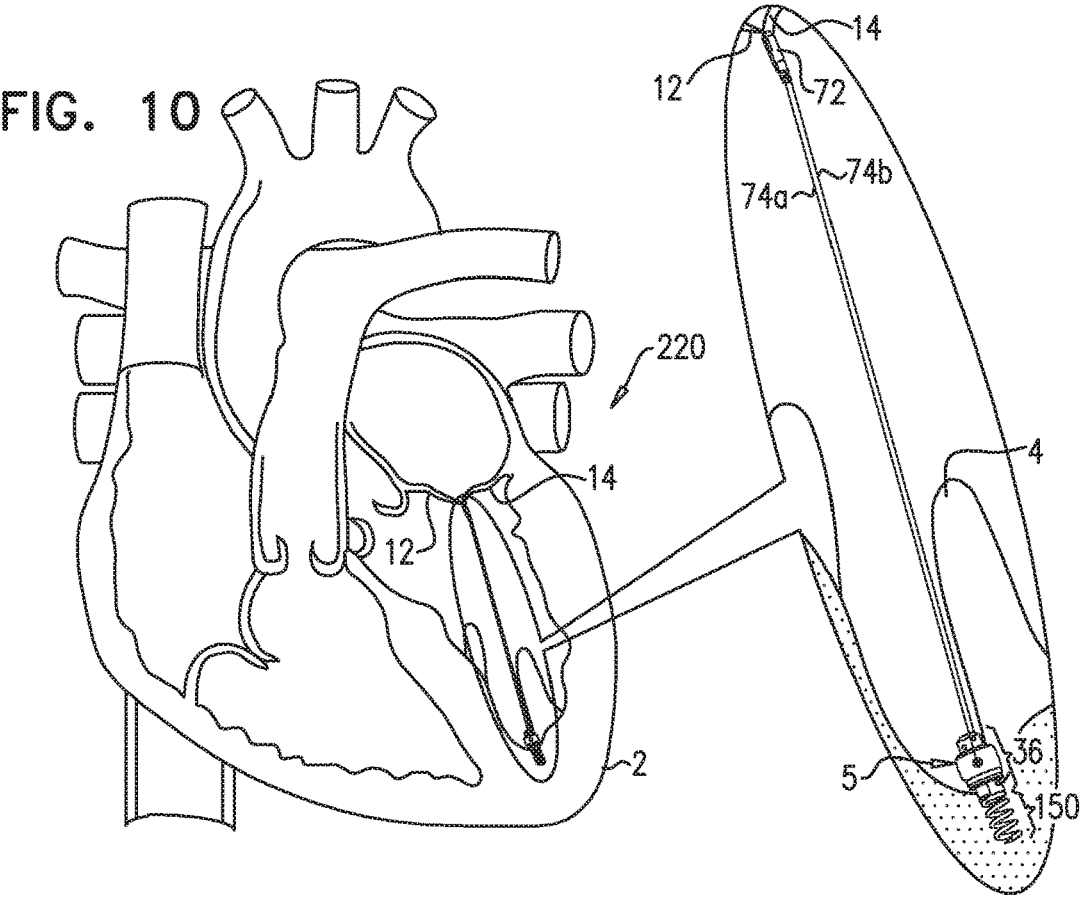

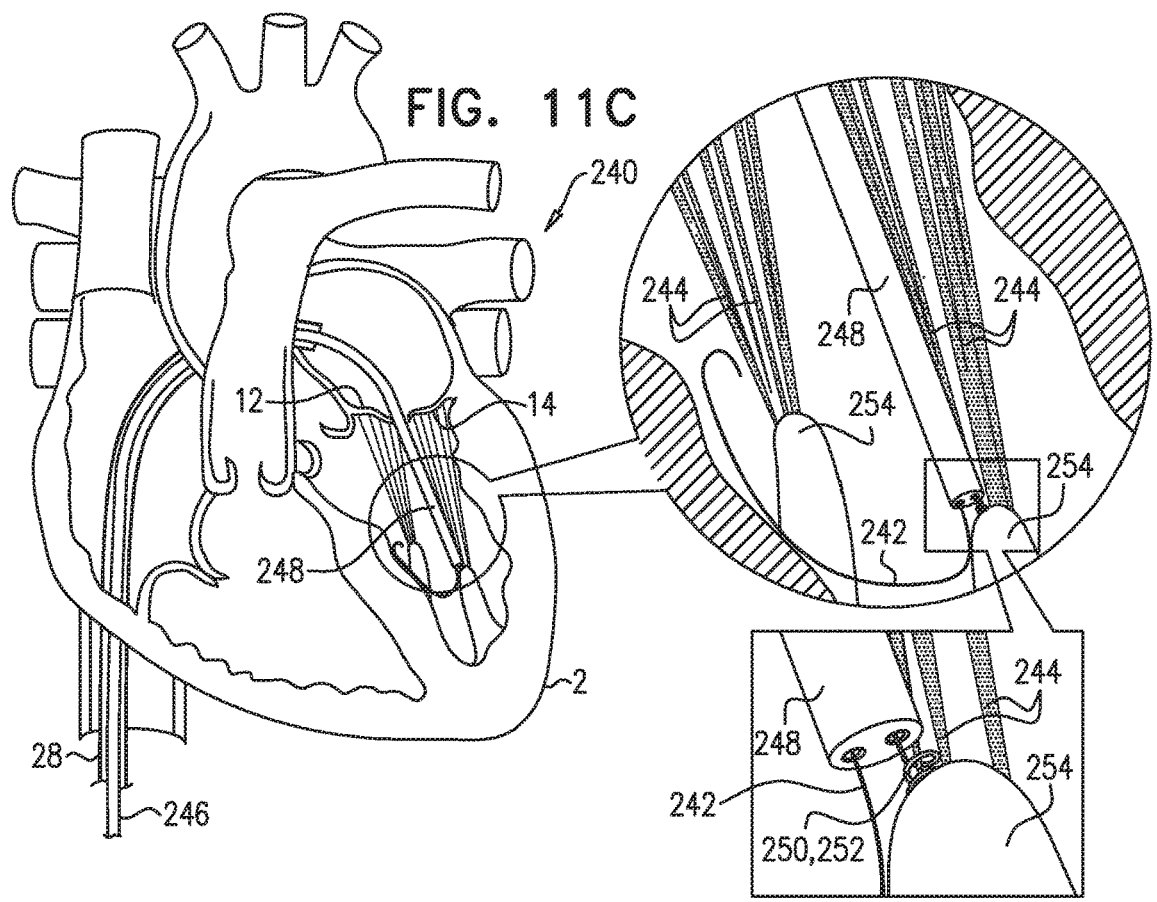
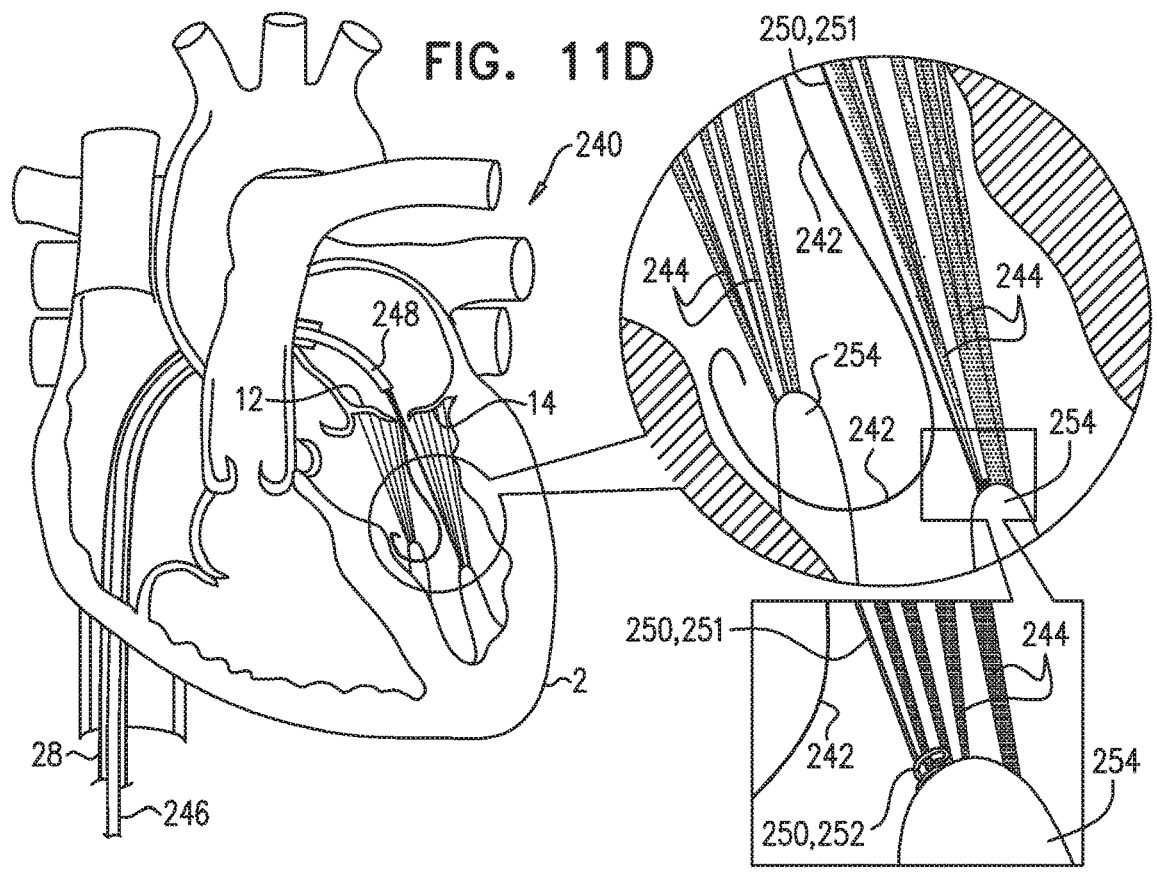

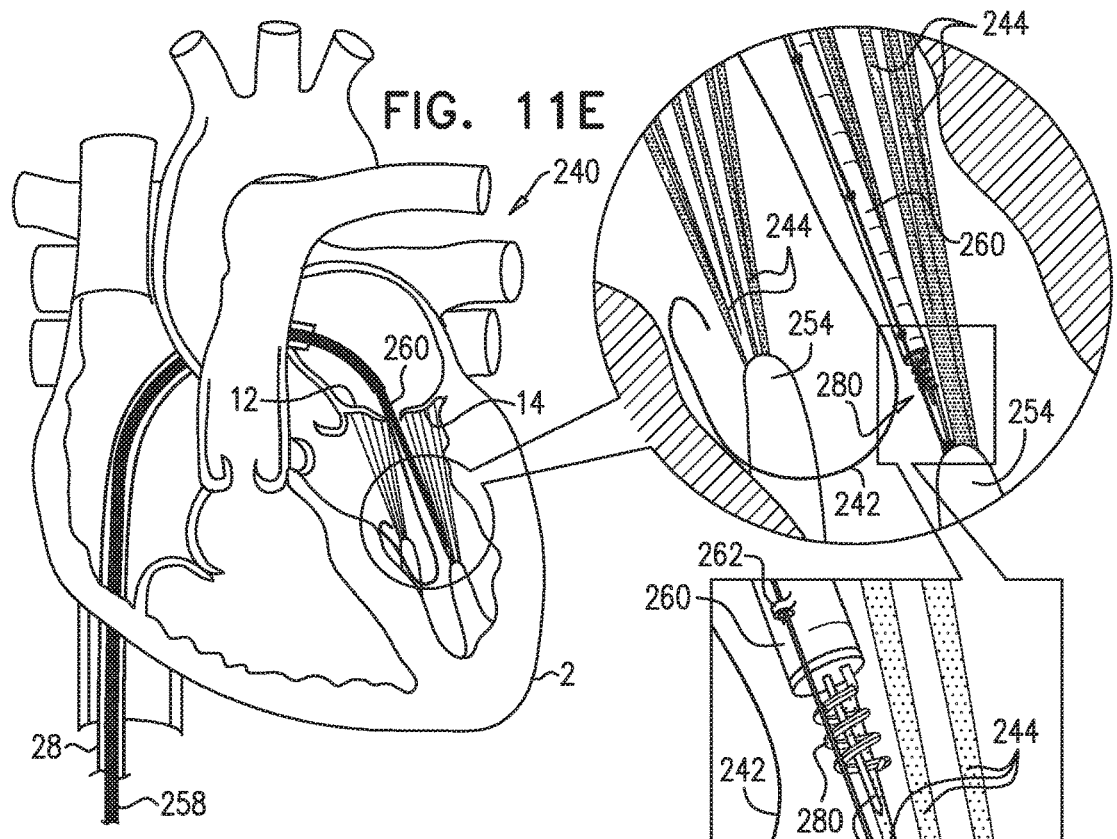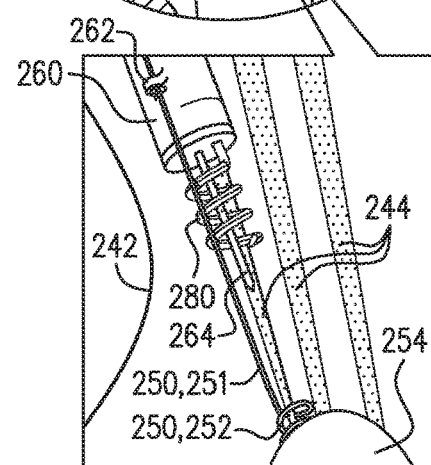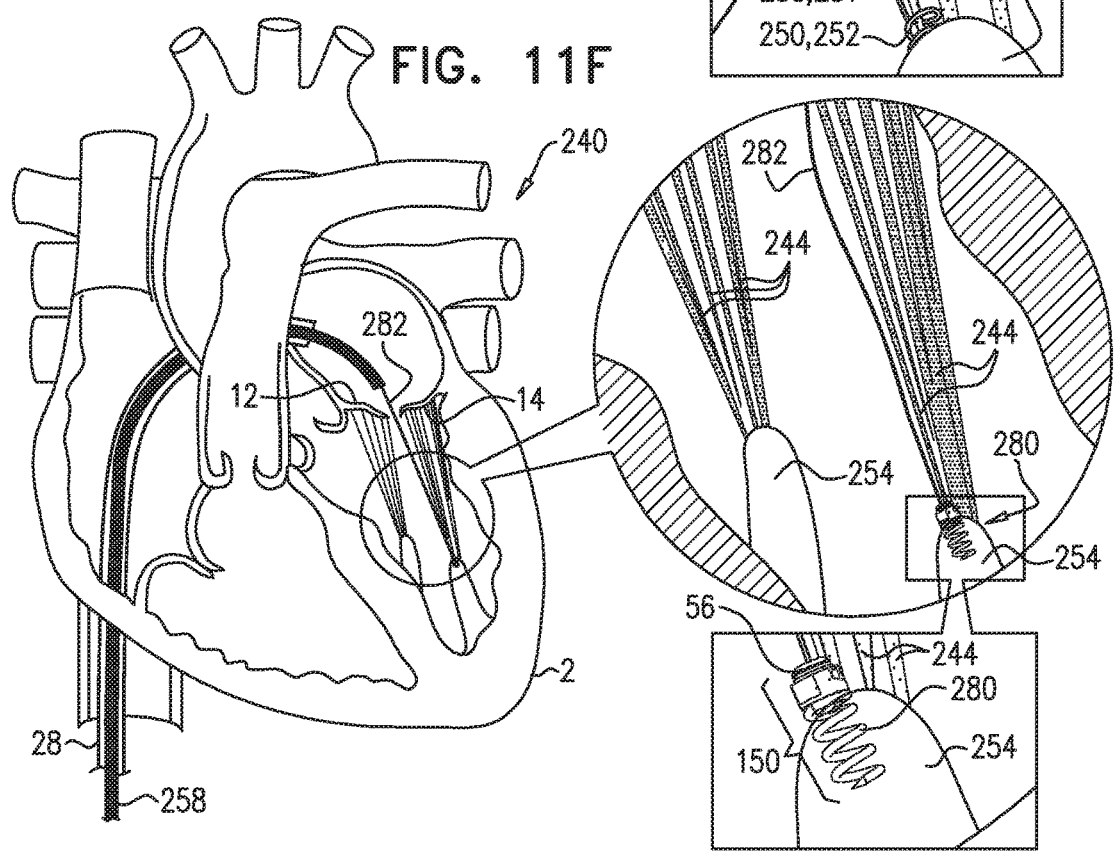

TECHNIQUES FOR GUIDED ADVANCEMENT OF A TOOL

CROSS-REFERENCES TO RELATED APPLICATIONS

The present application is a Continuation of U.S. Ser. No. 15/669,003 to Reich et al., filed Aug. 4, 2017, and entitled "Techniques for guide-wire based advancement of a tool," which published as US 2017/0325958, and which is a Divisional of U.S. Ser. No. 14/650,114 to Reich et al., filed Jun. 5, 2015, and entitled "Techniques for guide-wire based advancement of a tool," which published as US 2015/0297212 (now U.S. Pat. No. 9,730,793), and which is the US National Phase of PCT application IL2013/050992 to Reich et al., filed Dec. 3, 2013, and entitled "Techniques for guide-wire based advancement of a tool," which published as WO 2014/087402, and which claims priority from U.S. Provisional Patent application 61/733,979 to Reich et al., filed Dec. 6, 2012, and entitled "Techniques for guide-wire based advancement of a tool."

The present application is related to:

(a) International Application PCT/IL2011/000446 to Miller et al., entitled "Apparatus and method for guide-wire based advancement of a rotation assembly," filed on Jun. 6, 2011 (which published as WO/2011/154942);

(b) U.S. patent application Ser. No. 12/795,192 to Miller et al., entitled "A method for guide-wire based advancement of a rotation assembly," filed on Jun. 7, 2010 (which published as US 2011/0301698) (now U.S. Pat. No. 8,690,939);

(c) U.S. patent application Ser. No. 12/795,026 to Miller et al., entitled "Apparatus for guide-wire based advancement of a rotation assembly," filed on Jun. 7, 2010 (which published as US 2011/0106245) (now U.S. Pat. No. 8,940,042), which is a continuation-in-part of U.S. patent application Ser. No. 12/608,316 to Miller et al., entitled, "Tissue anchor for annuloplasty device," filed on Oct. 29, 2009 (now U.S. Pat. No. 8,277,502); and (d) U.S. patent application Ser. No. 13/707,013 to Reich et al., entitled "Apparatus and method for guide-wire based advancement of a rotation assembly", filed on Dec. 6, 2012 (which published as US 2013/0096672) (now U.S. Pat. No. 9,180,007).

All of these applications are incorporated herein by reference.

FIELD OF THE INVENTION

The present invention relates in general to valve and chordae tendineae repair. More specifically, the present invention relates to repair of an atrioventricular valve and associated chordae tendineae of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

Chronic or acute left ventricular dilatation can lead to papillary muscle displacement with increased leaflet tethering due to tension on chordae tendineae, as well as annular dilatation.

SUMMARY OF THE INVENTION

In some applications of the present invention, apparatus is provided comprising an implant comprising one or more primary adjustable repair chords and an adjustment mechanism that is configured to adjust a tension of the one or more adjustable repair chords and that is slidable along a guidewire toward an implantation site. Additionally, the apparatus comprises a first tissue-engaging element (e.g., a tissue anchor) that comprises one or more docking stations. Further additionally, in accordance with some applications of the present invention, a method is provided for implanting such apparatus. A respective guidewire is reversibly coupled to each one of the docking stations. The adjustment mechanism is slidable along the guidewire toward one of the one or more docking stations, and is coupled to the tissue-engaging element via the docking station. Thus, the docking station is a coupling element that provides coupling between two other elements (in this case, between adjustment mechanism and the tissue-engaging element.)

The repair chord comprises a flexible, longitudinal member (e.g., sutures or wires). The repair chord is coupled at a distal portion thereof to the adjustment mechanism. In some applications, the repair chord functions as artificial chordae tendineae. In other applications, the repair chord is used to adjust a distance between two portions of the ventricular wall. For some applications, the repair chord is coupled at a proximal portion thereof to a second tissue-engaging element (e.g., a tissue anchor which penetrates or clips a portion of tissue).

For other applications, the repair chord comprises a cord that is disposed within at least a portion of an annuloplasty ring structure (e.g., a full annuloplasty ring or a partial annuloplasty ring). For such applications, the annuloplasty ring structure comprises the adjustment mechanism that is coupled to the repair cord. The annuloplasty ring structure is slidable along the guidewire toward one of the one or more docking stations, and is coupled to the tissue-engaging element via the docking station. It is to be noted that the annuloplasty ring structure may be provided independently of the adjustment mechanism and the repair chord. For such applications, the annuloplasty ring structure is slidable along the guidewire toward one of the one or more docking stations, and is coupled to the tissue-engaging element via the docking station.

For yet other applications, a prosthetic heart valve and/or a support for the prosthetic heart valve is slidable along the guidewire toward one of the one or more docking stations, and is coupled to the tissue-engaging element via the docking station.

Thus, the tissue-engaging element and the docking station are used to facilitate implantation of an implant such as cardiac valve implants, namely annuloplasty ring structures, prosthetic valves, and/or apparatus for receiving a prosthetic valve (e.g., a docking station or a support for receiving the prosthetic valve).

Typically, during a transcatheter procedure, the first tissue-engaging element is coupled to a first portion of tissue at a first implantation site in a heart of a patient. The adjustment mechanism is then slid along the guidewire and toward the first tissue-engaging element at the first implantation site. The proximal portion of the repair chord is then coupled via the second tissue-engaging element to a second portion of tissue at a second implantation site. Following the coupling of the second tissue-engaging element to the second implantation site, the adjustment mechanism is further slid distally toward the first tissue-engaging element and is then coupled to the first tissue-engaging element via the one or more docking stations on the first tissue-engaging element. Following the coupling of the adjustment mechanism to the second tissue-engaging element, a length and tension of the repair chord is then adjusted in order to adjust a distance between the first and second implantation sites. For applications in which the repair chord functions as an artificial chordae tendineae, the adjustment of the length and tension of the repair chord draws the leaflets together, and/or pulls the leaflet down toward the first implantation site to repair the valve.

In some applications of the present invention, the adjustment mechanism comprises a spool assembly which adjusts a degree of tension of the repair chord. The spool assembly comprises a housing, which houses a spool to which a distal portion of the repair chord is coupled.

For applications in which the repair chord is coupled to two respective portions of the ventricular wall, the two portions are drawn together, thereby restoring the dimensions of the heart wall to physiological dimensions, and drawing the leaflets toward one another.

In some applications of the present invention, the adjustment mechanism comprises a reversible locking mechanism which facilitates bidirectional rotation of the spool in order to effect both tensioning and relaxing of the repair chord. That is, the spool is wound in one direction in order to tighten the repair chord, and in an opposite direction in order to slacken the repair chord. Thus, the spool adjustment mechanism facilitates bidirectional adjustment of the repair chord.

In some applications of the present invention, the adjustable repair chord is implanted during an open-heart or minimally-invasive procedure. In these applications, the delivery tool comprises a handle and a multilumen shaft that is coupled at a distal end thereof to the adjustment mechanism. The delivery tool functions to advance the adjustment mechanism to the first portion of tissue, implant the adjustment mechanism at the first portion of tissue, and effect adjustment of the repair chord by effecting rotation of the spool. For applications in which the repair chord functions as an artificial chordae tendineae, prior to implantation of the adjustment mechanism, the distal portion of the delivery tool and the adjustment mechanism coupled thereto are advanced between the leaflets of the atrioventricular valve and into the ventricle toward the first portion of tissue. The incision made in the heart is then closed around the delivery tool and the heart resumes its normal function during the adjustment of the length of the artificial chordae tendineae.

In some applications of the present invention, apparatus and method described herein may be used for providing artificial chordae tendineae in a left ventricle of the heart and effecting adjustment thereof. In some applications, apparatus and method described herein may be used for providing artificial chordae tendineae in a right ventricle of the heart and effecting adjustment thereof. In some applications, apparatus and method described herein may be used for providing a system to adjust a length between two portions of the heart wall. For other applications apparatus and method described herein may be used for providing a docking station for an annuloplasty ring or for a prosthetic valve.

In some applications of the present invention, a guide member, comprising a chord-engaging element that is slidably couplable to chordae tendineae of the patient is used to guide a deployment tool to a papillary muscle of the patient, so as to facilitate anchoring of a tissue anchor (e.g., a tissue anchor of a docking assembly) to the papillary muscle.

There is therefore provided, in accordance with an application of the present invention, apparatus for facilitating anchoring of a tissue anchor to a papillary muscle of a heart of a subject, the papillary muscle being coupled to one or more chordae tendineae of the heart of the subject, the apparatus being configured to be used with a guidewire, and including:

a housing, percutaneously deliverable to the heart of the subject, slidable along the guidewire, and shaped to define at least one opening;

a guide member, percutaneously deliverable to the heart of the subject, percutaneously removable from the subject, couplable to the housing, and having:
  a distal portion, including a chord-engaging element, configured to be percutaneously slidably coupled to at least one of the one or more chordae tendineae, and decouplable from the at least one of the one or more chordae, and
  a proximal portion, including a longitudinal element; and a deployment tool, configured (1) to be reversibly coupled to the anchor, (2) to be slidably coupled to the longitudinal element of the guide member, and (3) to anchor the tissue anchor to the papillary muscle of the subject.

In an application, the housing is configured to be decoupled from the guide member before the deployment tool is coupled to the guide member.

In an application, the tissue anchor includes a helical tissue anchor, and the deployment tool is configured to anchor the tissue anchor to the papillary muscle of the subject by rotating the tissue anchor.

In an application, the deployment tool includes a lance, configured to stabilize the deployment tool at the papillary muscle of the subject by penetrating tissue of the papillary muscle.

In an application, the lance is retractable into the deployment tool.

In an application, the apparatus further includes the anchor.

In an application, the guidewire includes a first guidewire, and the apparatus further includes a second guidewire, reversibly coupled to the anchor.

In an application, the apparatus further includes the guidewire, the guidewire being configured to be transluminally advanced to a vicinity of the one or more chordae tendineae of the subject.

In an application, the guidewire is configured to be transluminally advanced such that a distal portion of the guidewire is disposed between at least two chordae tendineae of the subject, the one or more chordae tendineae including at least one of the at least two chordae tendineae of the subject.

In an application, the housing is shaped to define a channel therethrough, the housing being slidable along the guidewire by the guidewire being slidable through the channel.

In an application, the chord-engaging element includes a helical element, configured to be housed by the housing, to be advanced out of the housing, and to form a helix outside of the housing.

In an application, the chord-engaging element is configured to be generally straight when housed by the housing, and to curl into the helix outside of the housing.

In an application, the chord-engaging element is configured to be helical when housed by the housing.

There is further provided, in accordance with an application of the present invention, a method for use with a papillary muscle of a heart of a subject, the papillary muscle being coupled to one or more chordae tendineae of the heart of the subject, the method including:

advancing a guide member to the chordae tendineae, the guide member having a proximal portion that includes a longitudinal element, and a distal portion that includes a chord-engaging element, configured to be slidably coupled to the chordae tendineae;

coupling the chord-engaging element to at least one of the one or more chordae tendineae;

sliding the chord-engaging element over the at least one of the chordae tendineae toward the papillary muscle; and advancing a tool toward the papillary muscle of the subject by sliding the tool along the longitudinal element.

In an application, the chord-engaging element includes a helical chord-engaging element, and coupling the chord-engaging element to the at least one of the chordae tendineae includes wrapping the helical chord-engaging element around the at least one of the chordae tendineae.

In an application, the method further includes, following the step of advancing, anchoring a tissue anchor to ventricular muscle tissue using the tool.

In an application, anchoring the tissue anchor includes anchoring the tissue anchor to ventricular muscle tissue in a vicinity of the papillary muscle.

In an application, anchoring the tissue anchor includes anchoring the tissue anchor to ventricular muscle tissue within 1 cm of the papillary muscle.

In an application, anchoring the tissue anchor includes anchoring the tissue anchor to the papillary muscle.

In an application, anchoring the tissue anchor includes anchoring a tissue anchor that is reversibly couplable to a guidewire.

In an application, the deployment tool includes a lance, and the method further includes, prior to anchoring the tissue anchor, stabilizing the tool with respect to the ventricular muscle tissue by penetrating the ventricular muscle tissue with the lance.

In an application, the method further includes retracting the lance into the deployment tool.

In an application, the step of advancing includes advancing, to the heart of the subject, a housing that is slidable along the guide member.

In an application, the method further includes, prior to the step of advancing, advancing a guidewire to a ventricle of the heart, and advancing the housing includes sliding the housing over the guidewire.

In an application, advancing the guidewire includes advancing a distal portion of the guidewire between at least two of the chordae tendineae of the subject.

In an application, the method further includes, subsequent to the step of advancing, sliding the chord-engaging element distally out of the housing.

In an application, the method further includes, subsequent to the step of coupling and prior to the step of advancing, proximally withdrawing the housing and decoupling the housing from the guide member while maintaining the coupling of the chord-engaging element to the at least one of the one or more chordae tendineae.

In an application, sliding the chord-engaging element distally out of the housing includes facilitating transitioning of the chord-engaging element from a generally straight state into a helical state.

There is further provided, in accordance with an application of the present invention, a method for use with a tissue anchor and a papillary muscle of a heart of a subject, the papillary muscle being coupled to one or more chordae tendineae of the heart of the subject, the method including:

percutaneously advancing to the chordae tendineae, along a guidewire that has been advanced to the chordae tendineae of the subject, a housing, shaped to define at least one opening;

advancing a distal portion of a guide member out of the opening of the housing, the distal portion of the guide member including a chord-engaging element;

coupling the chord-engaging element to at least one of the one or more chordae tendineae;

exposing a proximal portion of the guide member out of the opening of the housing by withdrawing the housing proximally with respect to the guide member, the proximal portion of the guide member including a longitudinal element; and anchoring the tissue anchor to ventricular muscle tissue of the subject by advancing a deployment tool, reversibly couplable to the tissue anchor, along the longitudinal element.

In an application, the method further includes, subsequently to the step of coupling and prior to the step of anchoring, sliding the chord-engaging element along the at least one chordae tendineae toward the papillary muscle.

In an application, the method further includes decoupling the housing from the guide member before advancing the deployment tool along the longitudinal member.

In an application, the tissue anchor includes a helical tissue anchor, and anchoring the tissue anchor includes rotating the tissue anchor.

In an application, the guidewire includes a first guidewire, and anchoring the tissue anchor includes anchoring a tissue anchor that is reversibly couplable to a second guidewire.

In an application, anchoring the tissue anchor includes anchoring the tissue anchor to ventricular muscle tissue in a vicinity of the papillary muscle.

In an application, anchoring the tissue anchor includes anchoring the tissue anchor to ventricular muscle tissue within 1 cm of the papillary muscle.

In an application, anchoring the tissue anchor includes anchoring the tissue anchor to the papillary muscle.

In an application, the deployment tool includes a lance, and the method further includes, before anchoring the tissue anchor, stabilizing the deployment tool with respect to the ventricular muscle tissue by penetrating the ventricular muscle tissue with the lance.

In an application, the method further includes retracting the lance into the deployment tool.

In an application, the step of advancing includes advancing the chord-engaging element out of the opening of the housing such that the chord-engaging element forms a helix outside of the housing.

In an application, advancing the chord-engaging element out of the opening of the housing includes facilitating a transition of the chord-engaging member from a generally straight state into a helical state.

The present invention will be more fully understood from the following detailed description of applications thereof, taken together with the drawings, in which:

BRIEF DESCRIPTION OF THE DRAWINGS

FIGS. 7-9 are schematic illustrations of adjusting by the adjustment mechanism a length of a repair chord coupled to the adjustment mechanism, in accordance with some applications of the present invention;

FIG. 10 is a schematic illustration of the adjustment mechanism and the repair chord, in accordance with some other applications of the present invention; and FIGS. 11A-F are schematic illustrations of a system and techniques for use thereof, for delivering a tissue anchor to a papillary muscle of a subject, in accordance with some applications of the invention.

DETAILED DESCRIPTION OF EMBODIMENTS

Figure 1:
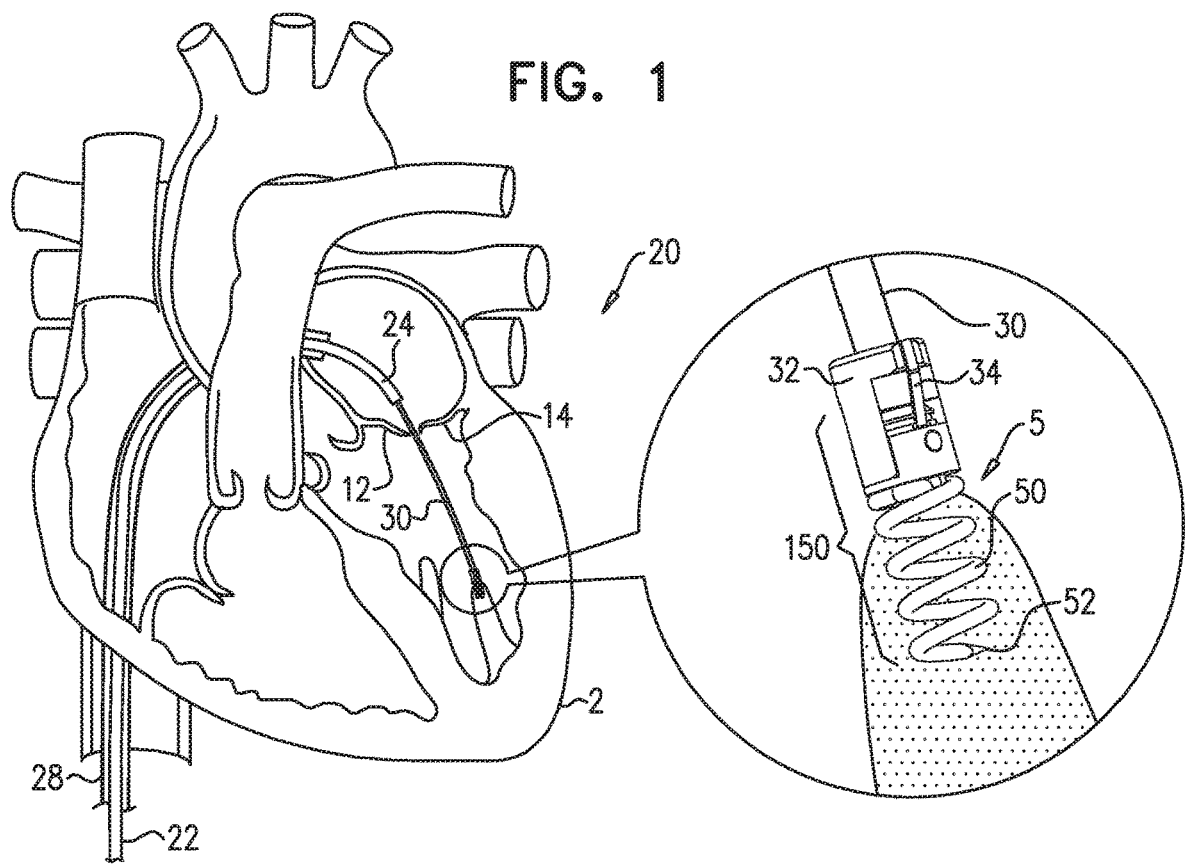
FIGS. 1-2 are schematic illustrations of apparatus comprising a tissue-engaging element comprising a docking station coupled to a guidewire, in accordance with some applications of the present invention.
Figure 2:
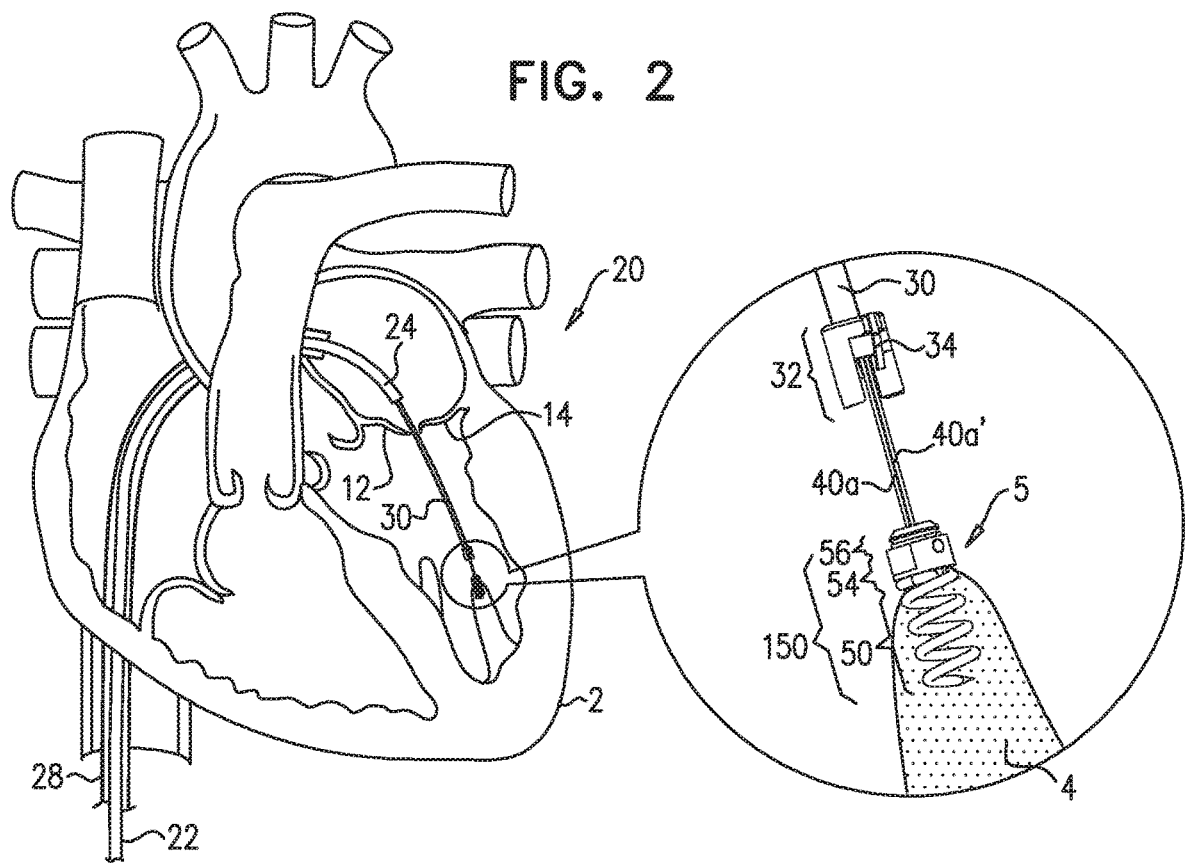

Reference is now made to FIGS. 1-2, which are schematic illustrations of a system 20 comprising a docking assembly 150 for implantation at a first implantation site 5 of a patient, in accordance with some applications of the present invention. As shown in FIG. 2, docking assembly 150 comprises a tissue-engaging element having (1) a distal portion comprising a tissue anchor 50 (e.g., a helical tissue anchor as shown by way of illustration and not limitation), and (2) a proximal portion comprising a docking platform 54, and at least one docking station 56. Thus, docking assembly 150 comprises (a) the distal portion which engages the tissue of the patient (i.e., the tissue-engaging element), and (b) the proximal portion which is coupled to docking station 56. At least one guide member, (e.g., a guidewire 40, shown in FIG. 2) is reversibly coupled to docking assembly 150 (e.g., by being looped around, or otherwise coupled to, a portion of assembly 150) so as to define first and second portions 40a and 40a' that extend away from assembly 150.

Tissue anchor 50 is typically implanted within cardiac tissue in a manner in which a distal portion of anchor 50 does not extend beyond an epicardium of heart 2 of the patient. Thus, anchor 50 is implanted at an intracardiac site such that the implant, (e.g., the adjustment mechanism or an implant comprising the adjustment mechanism) that is eventually coupled thereto (as described hereinbelow) is implanted at the intracardiac site such that no portions of the adjustment mechanism extend beyond the epicardium of the heart.

Docking assembly 150 and guidewire 40 are advanced toward implantation site typically during a transcatheter procedure, as shown. However, it is to be noted that the scope of the present invention includes the advancement of assembly 150 and guidewire 40 during a minimally-invasive or open-heart procedure. The procedure is typically performed with the aid of imaging, such as fluoroscopy, transesophageal echo, and/or echocardiography.

The transcatheter procedure typically begins with the advancing of a semi-rigid guidewire into a right atrium of the patient. The semi-rigid guidewire provides a guide for the subsequent advancement of a sheath 28 therealong and into the right atrium. For some applications, once sheath 28 has entered the right atrium, the semi-rigid guidewire is retracted from the patient's body. Sheath 28 typically comprises a 13-20 F sheath, although the size may be selected as appropriate for a given patient. Sheath 28 is advanced through vasculature into the right atrium using a suitable point of origin typically determined for a given patient. For example:

sheath 28 may be introduced into the femoral vein of the patient, through an inferior vena cava, into the right atrium, and into the left atrium transseptally, typically through the fossa ovalis;

sheath 28 may be introduced into the basilic vein, through the subclavian vein to the superior vena cava, into the right atrium, and into the left atrium transseptally, typically through the fossa ovalis; or sheath 28 may be introduced into the external jugular vein, through the subclavian vein to the superior vena cava, into the right atrium, and into the left atrium transseptally, typically through the fossa ovalis.

In some applications of the present invention, sheath 28 is advanced through the inferior vena cava of the patient (as shown) and into the right atrium using a suitable point of origin typically determined for a given patient.

Sheath 28 is advanced distally until the sheath reaches the interatrial septum. For some applications, a resilient needle and a dilator (not shown) are advanced through sheath 28 and into the heart. In order to advance sheath 28 transseptally into the left atrium, the dilator is advanced to the septum, and the needle is pushed from within the dilator and is allowed to puncture the septum to create an opening that facilitates passage of the dilator and subsequently sheath 28 therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 28 through the septum and into the left atrium is followed by the extraction of the dilator and the needle from within sheath 28. Subsequently, a docking-assembly delivery tool 30 is advanced through sheath 28. Tool 30 is typically advanced within a lumen of an advancement sheath 22 having a distal end 24. Advancement sheath 22 is advanced within sheath 28. Delivery tool 30 is coupled at a distal end thereof to a manipulator 32 which is reversibly coupled to docking station 56 and docking platform 54 of docking assembly 150. Manipulator 32 has (1) lateral arms which cup platform 54, and (2) a docking-station-coupler 34, as shown in FIG. 1. Coupler 34 is biased to move radially-inward, as shown in FIG. 1. Docking station 56 is ribbed, such that coupler 34, when moved radially inward, engages at least one rib of docking station 56, thereby coupling assembly 150 to delivery tool 30.

Delivery tool 30 and manipulator 32 are shaped so as to define a lumen for passage therethrough of guidewire 40.

Docking assembly 150 is implanted in implantation site 5 by rotating tool 30 in order to rotate anchor 50 and corkscrew anchor 50 into tissue of site 5. Site 5 typically comprises a portion of tissue at an intraventricular site in heart 2 of the patient. As shown, site 5 includes a papillary muscle 4, by way of illustration and not limitation. It is to be noted that site 5 includes any portion of cardiac tissue, e.g., a portion of a free wall of the ventricle, a portion of the septum facing the ventricle, a portion of tissue at a base of the papillary muscle, or a portion of the wall at the apex of the ventricle. (For the purposes of the claims, "a portion of tissue of a ventricle" includes any portion of cardiac tissue, e.g., a portion of a free wall of the ventricle, a portion of the septum facing the ventricle, a portion of tissue at a base of the papillary muscle, or a portion of the wall at the apex of the ventricle.)

Following the implantation of assembly 150 at site 5, tool 30 is disengaged from assembly 150 when the physician pulls on tool 30. This pulling pulls on manipulator 32 such that coupler 34 is actively moved radially outward against the ribs of docking station 56, and is thereby decoupled from station 56. At the time of pulling, tissue at implantation site 5 pulls on assembly 150 (in the direction opposite the direction of pulling by the physician) so as to help disengage tool 30 from assembly 150.

As shown in FIG. 2, following the decoupling of tool 30 from assembly 150, tool 30 is pulled proximally along guidewire 40 and is extracted from the body of the patient together with advancement sheath 22, leaving behind assembly 150 and guidewire 40.

Figure 3:
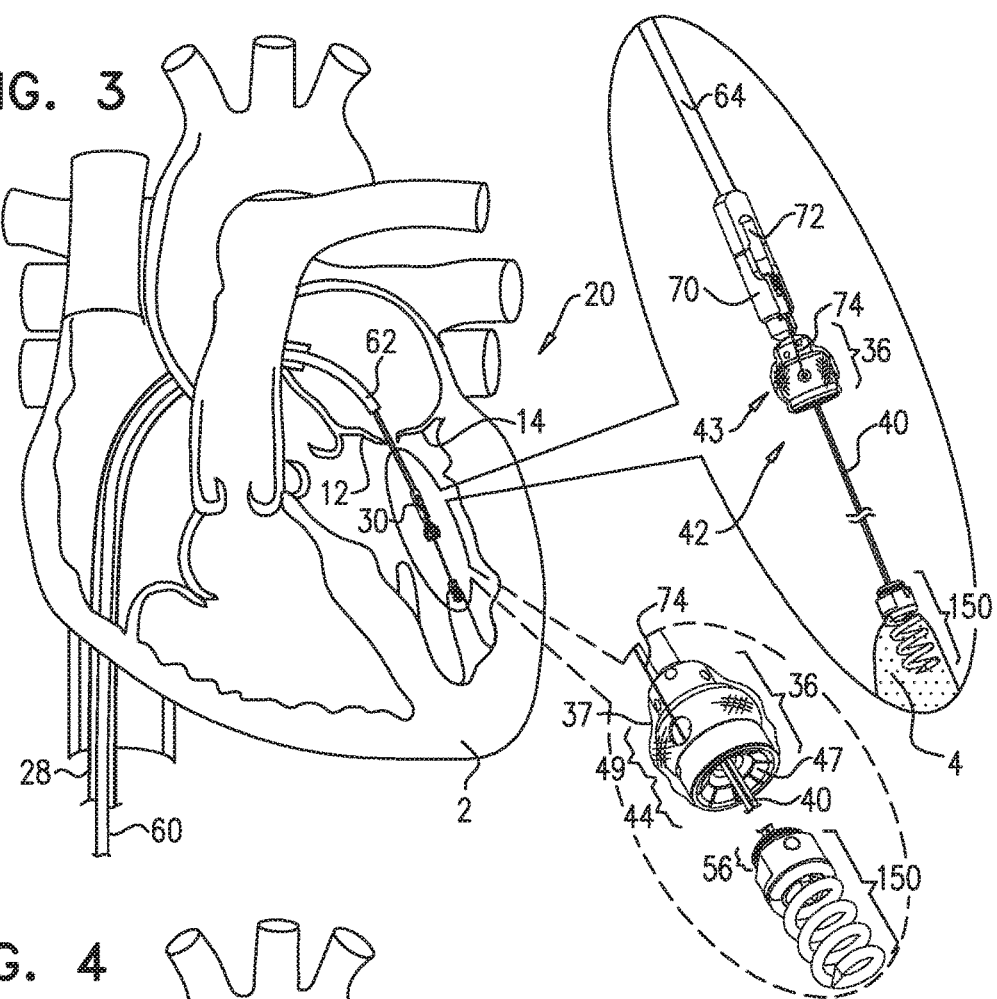
FIG. 3 is a schematic illustration of advancement of an adjustment mechanism along the guidewire toward the docking station of FIGS. 1 and 2, in accordance with some applications of the present invention.

FIG. 3 shows advancement of an implant (e.g., a spool assembly 36 comprising an adjustment mechanism 43) along guidewire 40 by an adjustment-mechanism delivery tool 64, in accordance with some applications of the present invention. Tool 64 is surrounded by and slidable within an advancement sheath 60 having a distal end 62.

Spool assembly 36 is surrounded by a braided fabric mesh, e.g., a polyester mesh, which promotes fibrosis around assembly 36 and facilitates coupling of assembly 36 to tissue of heart 2. Assembly 36 houses a rotatable structure (e.g., a spool as shown hereinbelow) that is surrounded by a housing 49. Housing 49 is coupled to a distal cap 44 which facilitates coupling of assembly 36 to docking station 56 of docking assembly 150. As shown, cap 44 is shaped so as to define a plurality of baffles 47 that are disposed angularly with respect to a distal end of cap 44. Baffles 47 are coupled to the distal end of cap 44 along respective coupling joints which facilitate movement of each baffle 47. During the coupling of spool assembly 36 to docking station 56, the ribbed portion of docking station 56 pushes inwardly baffles 47 of cap 44, as is described hereinbelow. Baffles 47 then expand and engage an area of docking station 56 between the ribs of the ribbed portion so as to dock and lock assembly 36 to docking station 56.

Additionally, cap 44 is shaped so as to define a central opening therethrough which facilitates passage therethrough of guidewire 40. Additionally, spool assembly 36 and the components thereof are shaped so as to define a central opening (i.e., an opening having the same axis as guidewire 40). That is, spool 46 has a central opening, and housing 49 has a central opening which facilitates passage of spool 46 and housing 49 along guidewire 40.

As shown, adjustment mechanism 43 is coupled to a distal portion of a repair chord 74 (e.g., repair chord 74 is looped through or otherwise coupled to a portion of adjustment mechanism 43). Chord 74 comprises a flexible longitudinal member. For some applications, and as is described hereinbelow, chord 74 functions as an artificial chordae tendineae. A proximal portion of chord 74 is coupled to a leaflet-engaging element 72 (e.g., a clip, as shown). Leaflet-engaging element 72 is disposed within a holder 70 that is coupled to delivery tool 64. Chord 74 a superelastic, biocompatible material (e.g., nitinol, ePTFE, PTFE, polyester, stainless steel, or cobalt chrome). Typically, chord 74 comprises an artificial chordae tendineae.

Figure 4:
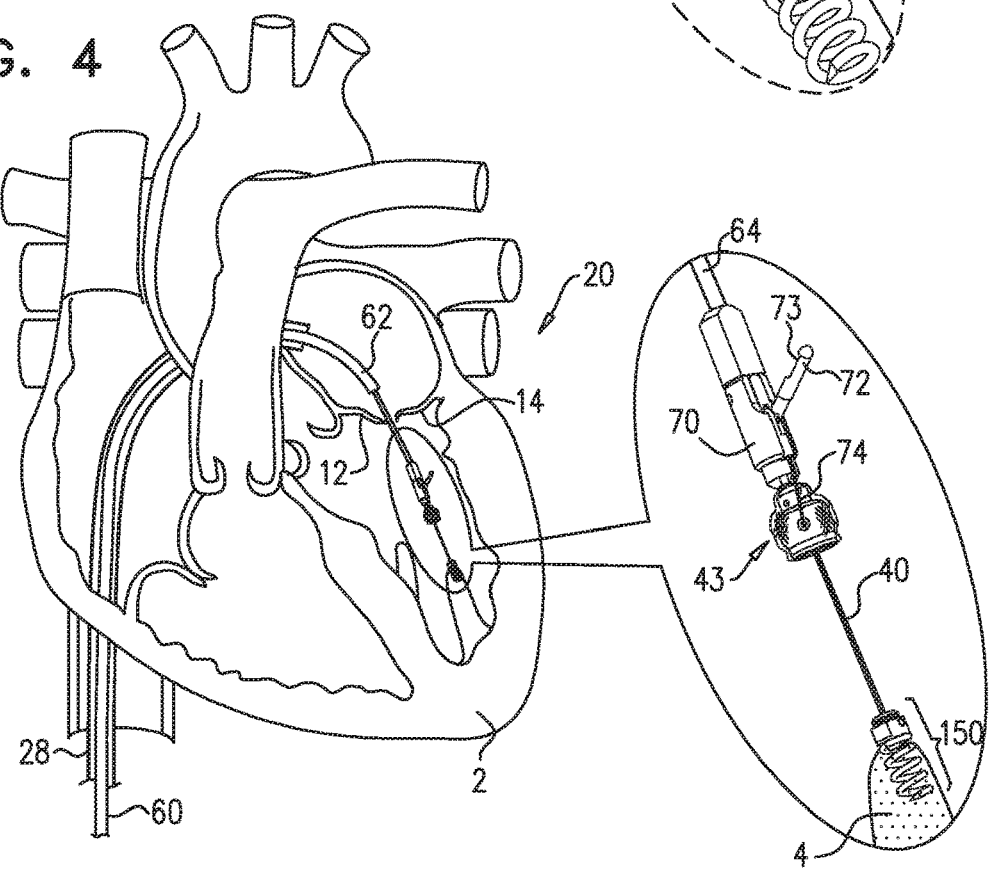
FIGS. 4-5 are schematic illustrations of engaging a leaflet with a leaflet engaging element, in accordance with some applications of the present invention.
Figure 5:
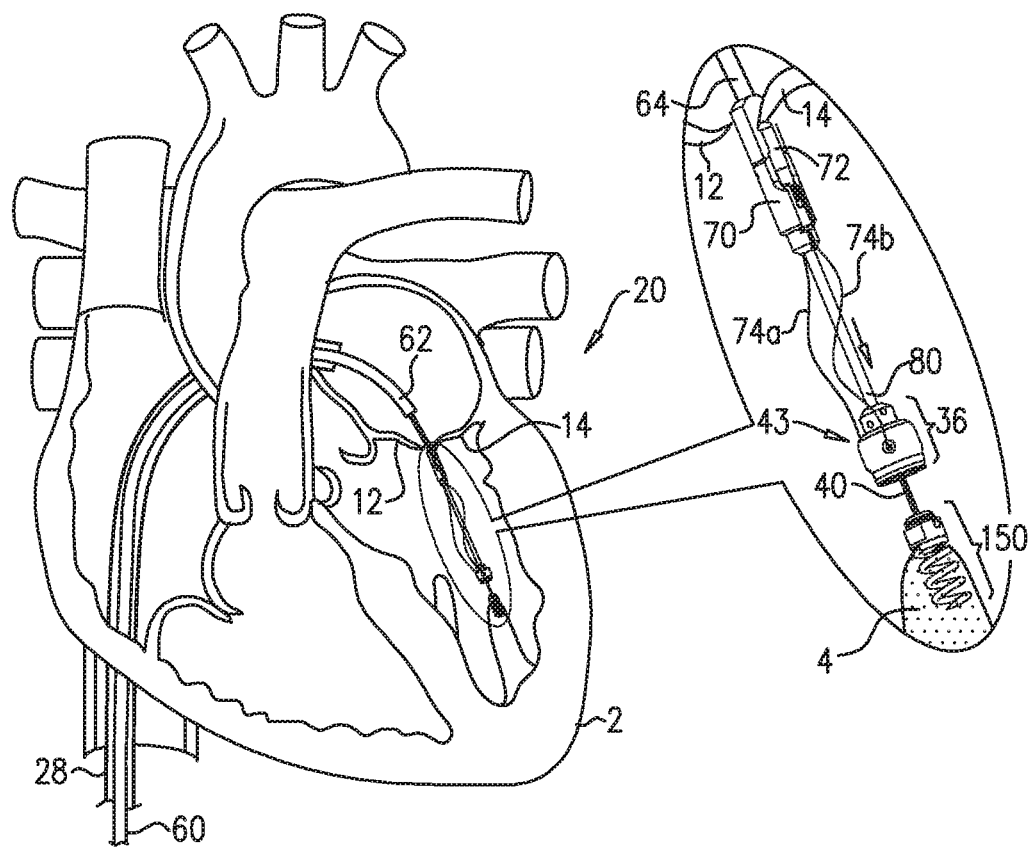

FIGS. 4-5 are schematic illustrations of the engaging of leaflet-engaging element 72 to at least one leaflet 14 of a mitral valve of the patient, in accordance with some applications of the present invention. As shown in FIG. 4, the clip is opened from a remote location outside the body of the patient.

For some applications, the clip typically is shaped so as to define at least one coupling protrusion 73. The clip has a tendency to close, and is initially held open by a cord (not shown) that is coupled to a surface of the clip, extends through delivery tool 64, and is held taught outside of the heart. Once the clip has been advanced to the desired location on the leaflet, the cord is relaxed, allowing the clip to close. The cord is removed, typically by releasing one end thereof and pulling the other end. The positioning of holder 70 between the leaflets (FIG. 5) helps ensure that the clip engages exactly one of the leaflets. It is noted that in FIG. 5 the clip is shown engaging only a single leaflet (leaflet 14). The clip typically engages the leaflet by clamping the leaflet such that the clip engages atrial and ventricular surfaces of the leaflet. The clip may puncture the leaflet, or may merely press firmly against the leaflet.

It is to be noted that the scope of the present invention include the clipping together of both leaflets 12 and 14. For applications in which system 20 is used to repair a tricuspid valve of the patient, the clip may clip any one, two, or all three leaflets together.

Holder 70 is shaped to define a groove which houses the clip during the advancement of tool 64 toward the ventricle. The groove functions as a track to facilitate slidable detachment of the clip from holder 70 following the engaging of the clip to leaflet 14.

Alternatively, the clip has a tendency to open. In order to close the clip, a cord is provided. A distal-most portion of the cord is looped around the clip. Once the clip has been advanced to the desired location on the leaflet, as shown in FIG. 5, the surgeon pulls on both ends of the cord, thereby causing the clip to become locked closed. The cord is removed, typically by releasing one end thereof and pulling the other end.

It is to be noted that the scope of the present invention includes any leaflet-engaging element known in the art.

As shown in FIG. 5, portions 74a and 74b extend from leaflet-engaging element 72 toward adjustment mechanism 43. Portions 74a and 74b define portions of a single chord 74 that is looped through a portion of mechanism 43. Alternatively, portions 74a and 74b represent two distinct chords which are coupled at their distal ends to adjustment mechanism 43 and at their proximal ends to leaflet-engaging element 72.

As shown, leaflet-engaging element 72 engages leaflet 14 prior to coupling spool assembly 36 to docking station 56.

Figure 6:
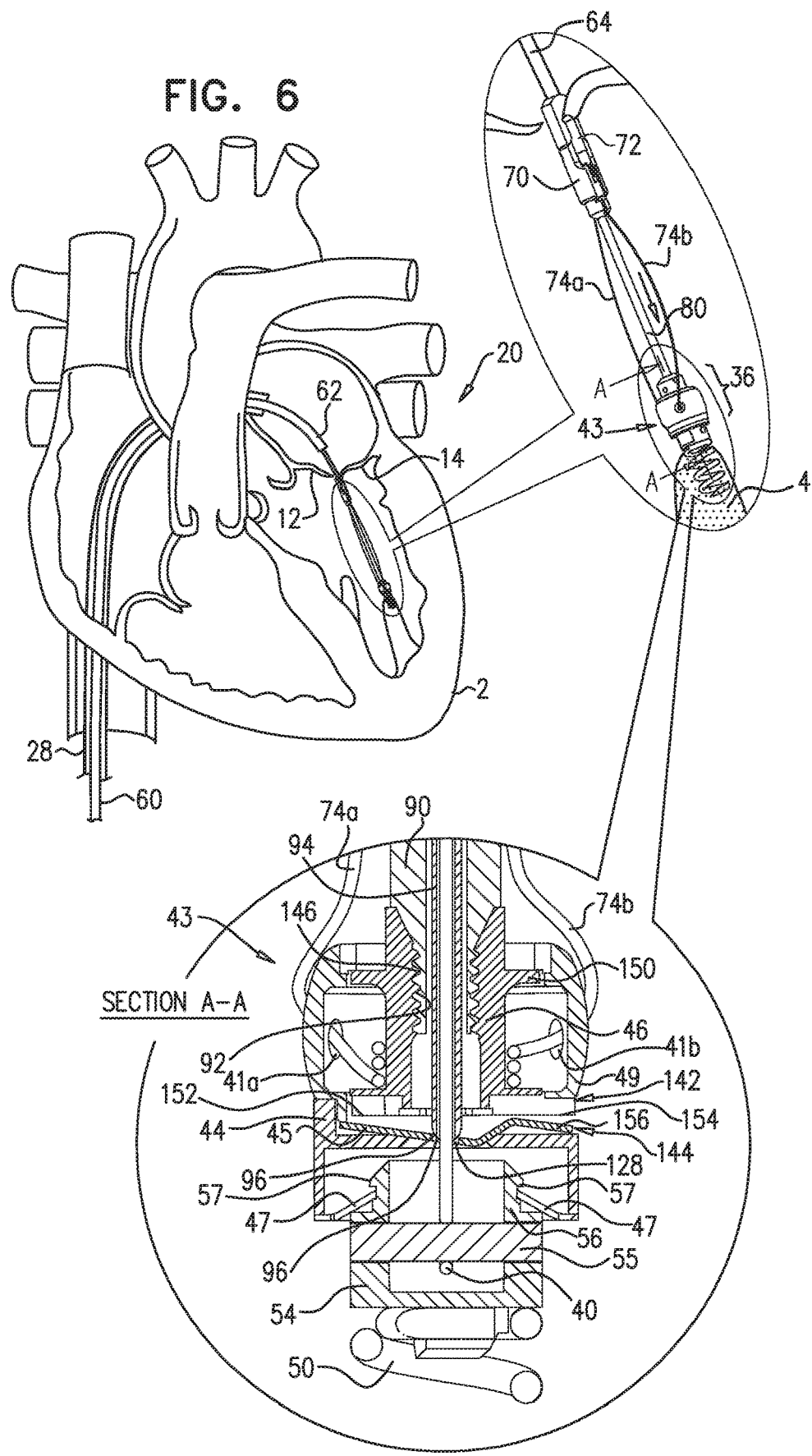
FIG. 6 is a schematic illustration of coupling of the adjustment mechanism of FIG. 3 to the docking station, in accordance with some applications of the present invention.

FIG. 6 shows spool assembly 36 being coupled to docking station 56, in accordance with some applications of the present invention. Following the coupling of leaflet-engaging element 72 to leaflet 14, spool assembly 36 is pushed distally toward docking station 56. Spool assembly 36 is coupled to an advancement shaft 80 which pushes assembly 36. Shaft 80 slides within a lumen of delivery tool 64 and within a lumen of holder 70 so as to advance spool assembly 36, while leaflet-engaging element 72 remains engaged with leaflet 14. Advancement shaft 80 functions to advance distally spool assembly 36 and functions to facilitate engagement between spool assembly 36 and docking station 56.

As described hereinabove, docking station 56 has one or more locking mechanisms (e.g., one or more ribs 57, shown in the enlarged cross-sectional image of FIG. 6) which project laterally such that rib 57 defines a shelf and an depressed area underneath the shelf (i.e., the cross-sectional diameter at rib 57 is larger than the cross-sectional diameter at the area underneath the shelf). As described hereinabove, cap 44 of assembly 36 is shaped so as to define a plurality of baffles 47. As cap 44 engages docking station 56, baffles 47 are pushed inward and upward angularly as each baffle slides against rib 57. After each baffle 47 passes the shelf of rib 57, the baffle engages the depressed area underneath the shelf of rib 57, as shown in the enlarged cross-sectional image of FIG. 6. The shelf of rib 57 prevents upward movement of baffles 47 and thereby locks in place baffles 47 and cap 44 with respect to docking station 56. Rib 57, therefore, comprises a locking mechanism so as to lock implant 42 (e.g., adjustment mechanism 43) to tissue anchor 50.

Following the coupling of assembly 36 to docking station 56, spool 46 is rotated in a first rotational direction in order to advance with respect to spool 46 and contact with spool 46 successive portions of chord 74. For example, when the successive portions of chord 74 are advanced with respect to spool 46, the successive portions of chord 74 are looped around spool 46. The rotating of spool 46 in the first rotational direction pulls tight and adjusts a length of chord 74 between leaflet 14 and spool 46, in order to adjust a distance between leaflet 14 and implantation site 5 and to facilitate coaptation between leaflets 12 and 14, as is described hereinbelow.

Housing 49 is shaped so as to provide openings 41a and 41b for passage therethrough of portions 74a and 74b, respectively, of chord 74 into housing 49. For some applications of the present invention, portions 74a and 74b define portions of a single chord 74 that is looped through spool 46. For other applications, portions 74a and 74b define discrete chords which are each coupled at respective distal ends thereof to spool 46.

The enlarged, cross-sectional image of FIG. 6 shows spool 46 within housing 49. Spool 46 defines an upper surface 150, a lower surface 152, and a cylindrical body portion disposed vertically between surfaces 150 and 152. Spool 46 is shaped to provide a driving interface, e.g., a channel, which extends from an opening provided by upper surface 150 to an opening provided by lower surface 152. A proximal portion of the driving interface is shaped to define a threaded portion 146 which may or may not be tapered. Threaded portion 146 of spool 46 is engageable by a threaded portion of a screwdriver head 92 of a screwdriver 90. Screwdriver 90 is coupled to a distal end of shaft 80. For some applications, shaft 80 rotates screwdriver 90. For other applications, shaft 80 is shaped so as to define a lumen for advancement therethrough of a screwdriver-rotation tool that facilitates rotation of screwdriver 90. Rotation of screwdriver 90 and screwdriver head 92 rotates spool 46, as the respective threaded portions of spool 46 and screwdriver head 92 engage. The cylindrical body portion of spool 46 is shaped to define one or more holes which function as respective coupling sites for coupling (e.g., looping through the one or more holes, or welding to spool 46 in the vicinity of the one or more holes) of any number of chords 74 to spool 46.

Lower surface 152 of spool 46 is shaped to define one or more (e.g., a plurality, as shown) recesses 154 which define structural barrier portions 155 of lower surface 152. It is to be noted that any suitable number of recesses 154 may be provided, e.g., between 1 and 10 recesses, circumferentially or otherwise, with respect to lower surface 152 of spool 46.

As shown, a locking mechanism 45 is disposed in communication with lower surface 152 of spool 46 and disposed in communication with at least in part to a lower surface of housing 49. Typically, a cap 44 maintains locking mechanism 45 in place with respect to lower surface 152 of spool 46 and lower surface of housing 49. For some applications, locking mechanism 45 is coupled, e.g., welded, to the lower surface of housing 49. Typically, locking mechanism 45 defines a mechanical element having a planar surface that defines slits. It is to be noted that the surface of locking mechanism 45 may also be curved, and not planar. Locking mechanism 45 is shaped to provide a protrusion 156 which projects out of a plane defined by the planar surface of the mechanical element. The slits of mechanism 45 define a depressible portion 128 that is disposed in communication with and extends toward protrusion 156. Depressible portion 128 is moveable in response to a force applied thereto typically by an elongate locking mechanism release rod 94 which slides through a lumen of screwdriver 90 and a torque-delivering tool that is coupled thereto.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

Cap 44 is provided that is shaped to define a planar surface and an annular wall having an upper surface thereof. The upper surface of the annular wall is coupled to, e.g., welded to, a lower surface provided by housing 49. The annular wall of cap 44 is shaped to define a recessed portion 144 of cap 44 that is in alignment with a recessed portion 142 of spool housing 49.

As shown, a distal end 96 of locking mechanism release rod 94 pushes distally on depressible portion 128 in order to unlock locking mechanism 45 from spool 46. Pushing depressible portion 128 by locking mechanism release rod 94 pushes distally protrusion 156 within recessed portion 142 of housing 49 and within recessed portion 144 of cap 44, which frees protrusion 156 from recesses 154 of spool 46. Once protrusion 156 is released from recesses 154 of spool 46, the physician is able to rotate spool 46 bidirectionally in order to adjust a tension of chord 74.

When the physician rotates spool 46 in the first rotational direction, chord 74 is pulled tight, and leaflet 14 is drawn toward adjustment mechanism 43 and toward anterior leaflet 12 of mitral valve 8.

In the resting state (i.e., prior to the rotation of spool 46 in order to adjust chord 74, following coupling of leaflet-engaging element 72 to leaflet 14) chord 74 is wrapped around spool 46 a few times (e.g., three times, by way of illustration and not limitation). This winding provides excess slack to chord 74 (in case portions 74a and 74b are coupled too tightly to leaflet 14). If the physician wishes to provide slack to chord 74 or to any one of portion 74a or 74b, the physician unwinds a bit of the wrapped portion of chord 74 from around spool 46 (e.g., by unwinding chord 74 a few times from around spool 46, or by unwinding chord 74 entirely from around spool 46 so that chord 74 slides freely through spool 46 within a channel provided therein). In order to accomplish such unwinding, the physician rotates spool 46 in a rotational direction in which it unwinds the wrapped portion of chord 74. Since chord 74 is looped through spool 46 in the channel provided therein, when chord 74 is unwound from spool 46, the physician can pull on one or both portions 74a and 74b so as to adjust, make even, or further slacken any one of or both portions 74a and 74b that extend from spool 46.

When the physician desires to pull tight chord 74, he or she effects rotation of spool 46 in a first rotational direction, i.e., the direction opposite the second rotational direction in which spool 46 is rotated during the unwinding of chord 74 from spool 46. Rotation of spool 46 in the first rotational direction winds chord 74 around spool 46, while rotation of spool 46 in a second rotational direction that is opposite the first rotational direction, unwinds the portion of longitudinal chord 74 from around spool 46.

Figure 7:
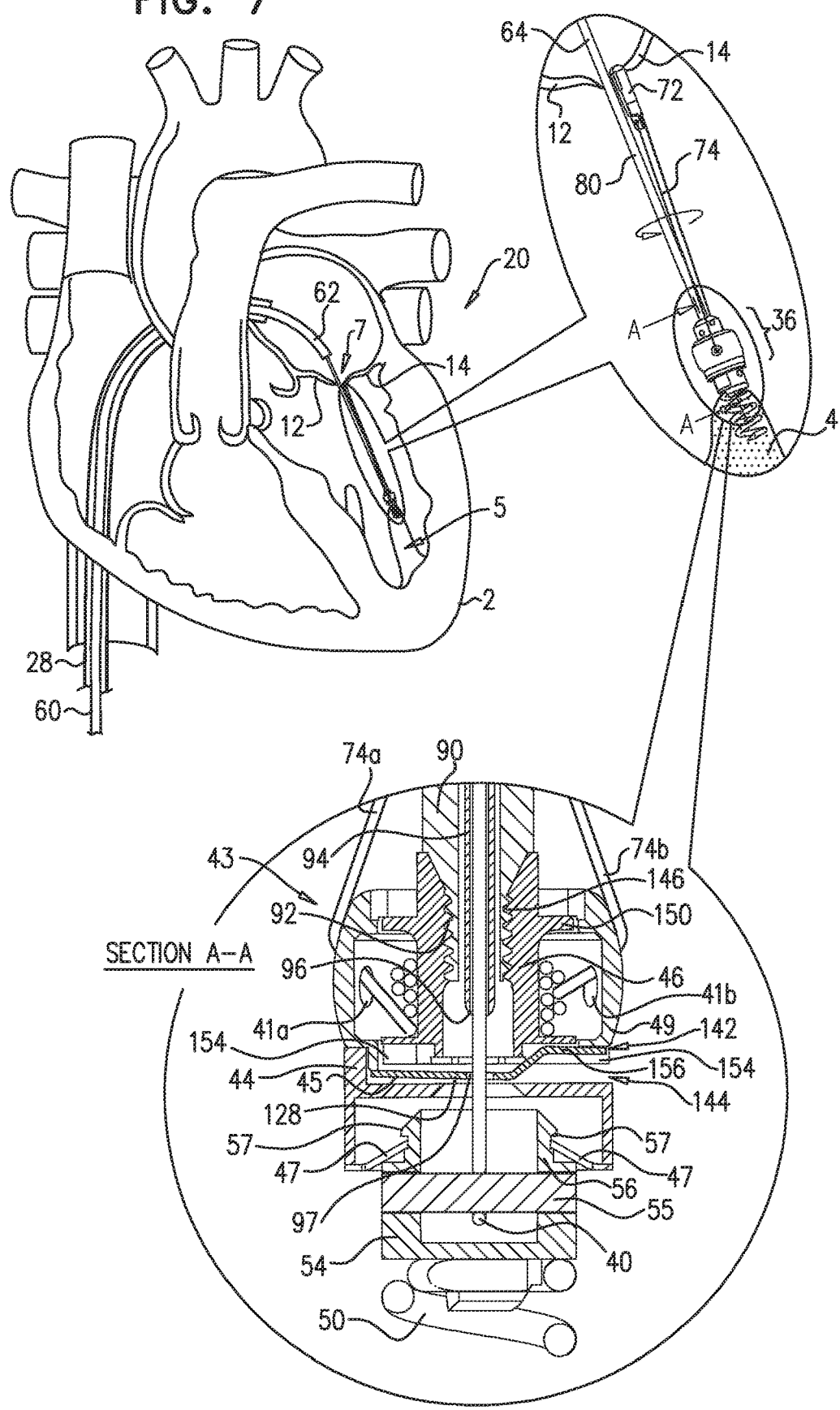

FIG. 7 shows spool assembly 36 following the adjustment of chord 74 by rotating screwdriver 90 in the direction as indicated by the arrow, and the partial removal of screwdriver 90, in accordance with some applications of the present invention. As shown in the enlarged cross-sectional image of FIG. 7, successive portions of chord 74 are wrapped around spool 46. That is, chord 74 is wrapped more times around spool 46 following adjustment (e.g., an additional 4 times, as shown in FIG. 7), than prior to adjustment (FIG. 6). This pulls chord 74 from a slackened state (FIG. 6) to a taut state (FIG. 7) in order to adjust a length of chord 74 between adjustment mechanism 43 and the proximal end of chord 74 that is coupled to leaflet-engaging element 72. Additionally, this applying of tension to chord 74 adjusts a length between first and second implantation sites 5 and 7. Typically, chord 74 is adjusted while heart 2 is beating.

As shown, rod 94 is shaped so as to define a central lumen and a distal opening for passage therethrough of guidewire 40. Additionally, depressible portion 128 is shaped so as to provide an opening for passage of guidewire 40 therethrough. Guidewire 40 is looped around a distal looping element 55 of docking platform 54 of docking assembly 150. Following the adjusting of the tension and length of chord 74, screwdriver 90 is decoupled from spool 46 (e.g., by being unscrewed from threaded portion 146 of spool 46) and is advanced proximally together with rod 94 away from spool assembly 36, as shown in the enlarged, cross-sectional image of FIG. 7.

Following the decoupling of screwdriver 90 from spool 46 and the removal of screwdriver 90, guidewire 40 remains coupled to docking platform 54 and docking assembly 150. Guidewire 40 then facilitates subsequent advancement of screwdriver 90 or any other tool to access spool assembly 36 and/or to facilitate further adjustment of chord 74 beyond the initial adjustment. Guidewire 40 may remain chronically coupled to docking assembly 150 and may be accessible at a subcutaneous location of the patient, e.g., a port. For other applications, guidewire 40 is removed from docking assembly 150 when the physician determines that further adjustment of chord 74 is not needed. The physician removes guidewire 40 by pulling, from outside the body of the patient, one end of guidewire 40 so that guidewire 40 slides around element 55 and is unlooped therefrom. The physician continues to pull on the end of guidewire 40 until the second end of wire 40 is exposed and removed from the patient.

Following the removal of locking-mechanism release rod 94, depressible portion 128 is no longer depressed by distal end 96 of rod 94, and protrusion 156 returns within a recess 154 of spool 46 so as to lock spool 46 in place and restriction rotation thereof in either direction (FIG. 7).

Reference is now made to FIGS. 3-7. It is to be noted that spool assembly 36 is only coupled to docking assembly 150 following the coupling of leaflet-engaging element 72 to leaflet 14. This is done in order to reduce the strain on implantation site 5. Should spool assembly 36 be implanted at implantation site 5 prior to engaging leaflet 14 with leaflet-engaging element 72, more strain would be applied to implantation site 5 than if spool assembly 36 had been implanted following the coupling of leaflet-engaging element 72 to leaflet 14, as described herein. That is, the pulling force is applied in a downward direction from leaflet 14 toward implantation site 5 instead of from implantation site 5 upward toward leaflet 14.

Figure 8:
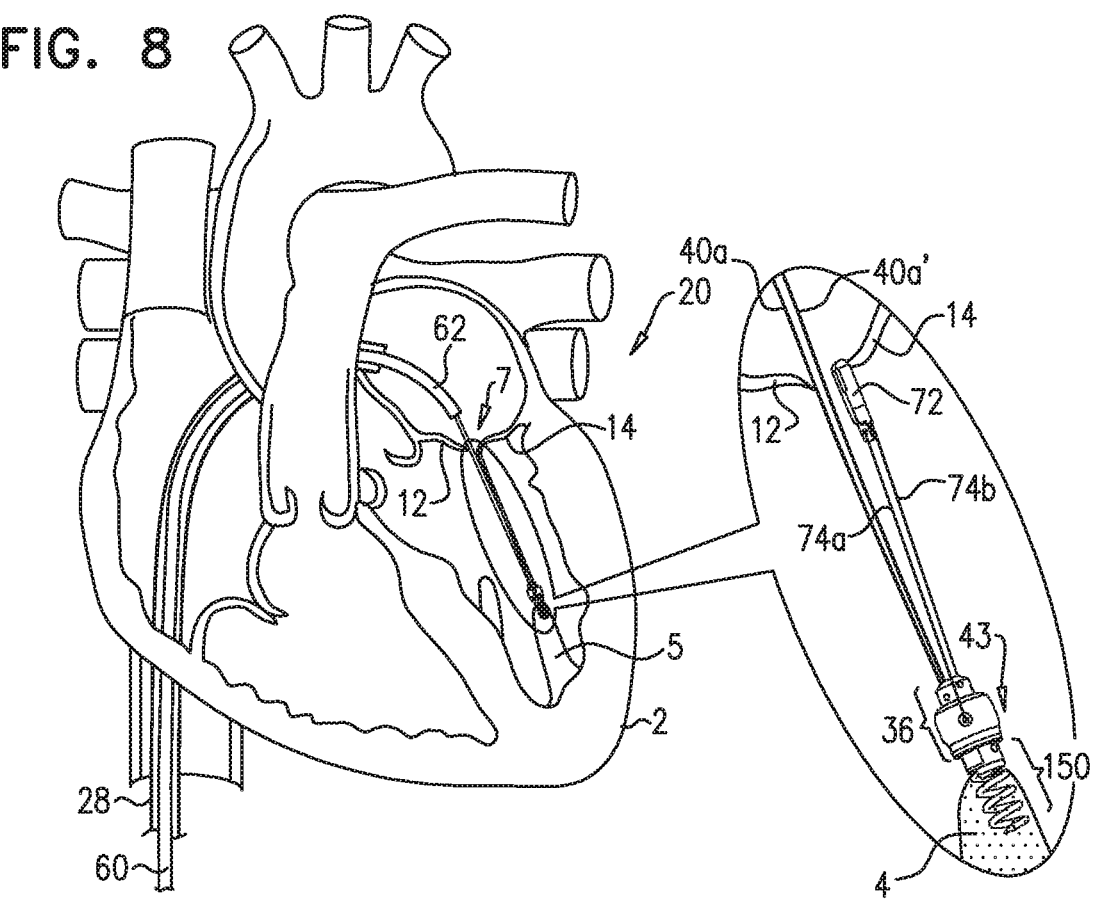

FIG. 8 shows system 20 following the removal of the tool used to rotate spool 46 of spool assembly 36, in accordance with some applications of the present invention. As shown, chord 74 is pulled tight such that its length and tension are adjusted, and leaflet 14 is pulled and adjusted commensurate with the adjustment of chord 74. Guidewire 40 remains coupled to spool assembly 36 and to docking assembly 150, as shown, such that portions 40a and 40a' extend from spool assembly 36. Guidewire 40 facilitates the reintroduction of the tool used to rotate spool 46, or of any other tool.

FIG. 9 shows system 20 following the removal of guidewire 40 from heart 2, in accordance with some applications of the present invention. As shown, the adjustment of chord 74 draws leaflets 12 and 14 together. It is to be noted that although leaflet-engaging element 72 is shown as engaging only leaflet 14, the scope of the present invention includes the engaging of both leaflets 12 and 14 by leaflet-engaging element 72.

FIG. 10 shows a system 220, as described hereinabove with reference to system 20, with the exception that implantation site 5 includes tissue of the wall of the ventricle at the base of papillary muscle 4 in a vicinity of the apex of the heart, in accordance with some applications of the present invention. Implantation site 5 is shown by way of illustration and not limitation, and as described hereinabove, site 5 may include any portion of tissue of heart 2. It is to be noted that although leaflet-engaging element 72 is shown as engaging only leaflet 14, the scope of the present invention includes the engaging of both leaflets 12 and 14 by leaflet-engaging element 72.

Reference is now made to FIGS. 11A-F, which are schematic illustrations of a system 240 and techniques for use thereof, for delivering a tissue anchor 280 to a papillary muscle of a subject, in accordance with some applications of the invention. For some applications of the invention, tissue anchor 280 comprises tissue anchor 50 of docking assembly 150, described hereinabove. Alternatively, tissue anchor 280 may comprise a different tissue anchor. Similarly, tissue anchor 280 may comprise a helical tissue anchor, as shown in FIGS. 11A-F by way of illustration and not limitation, or may comprise a different tissue anchor.

Figure 11A:
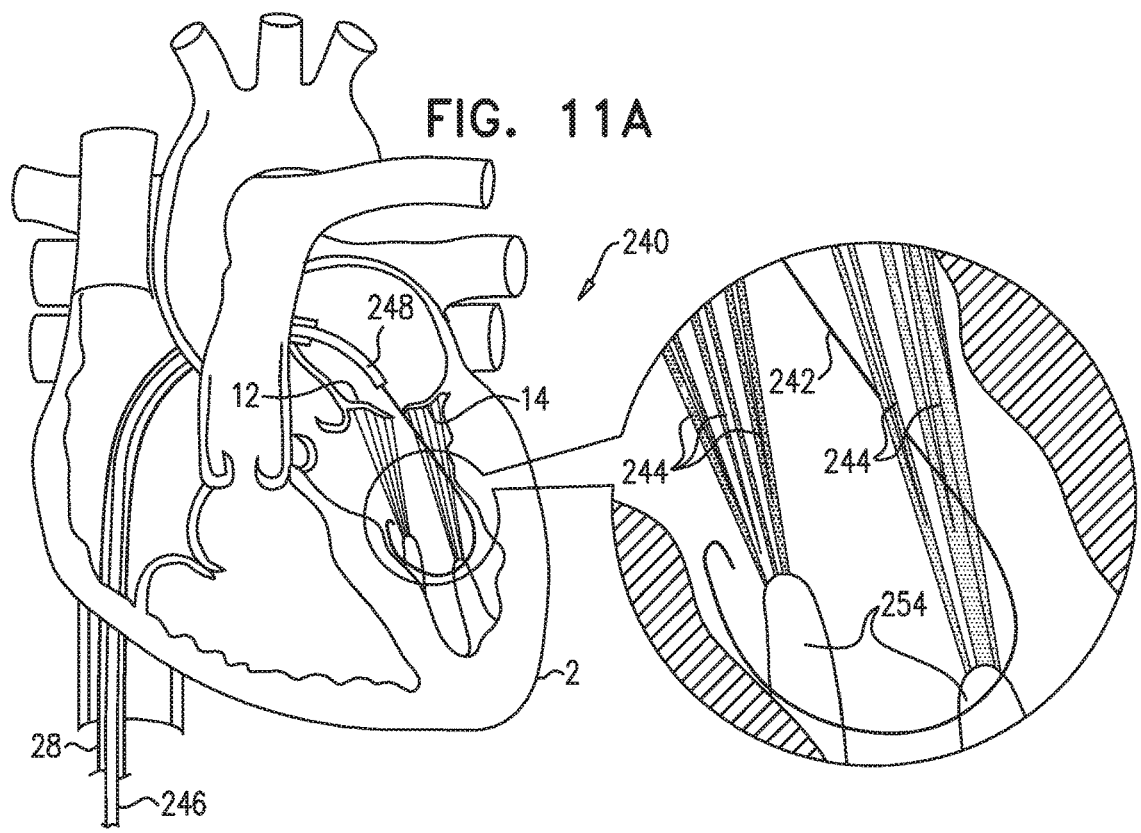

As described hereinabove (e.g., with reference to FIGS. 1-2), transcatheter access to heart 2 typically begins with the advancing of a semi-rigid guidewire into the left atrium of the patient, and sheath 28 is subsequently advanced along (e.g., over) the guidewire, to the left atrium. Typically, but not necessarily, this is performed using a standard transseptal puncture procedure, and further typically, the guidewire is advanced to the heart transfemorally, as shown. Alternatively, the guidewire may be advanced using a retrograde approach, via the aorta of the subject. Similarly, any suitable approach may be used such as, but not limited to, those described with reference to FIGS. 1-2. For some applications, such that those described with reference to FIGS. 11A-F, the guidewire is not immediately retracted from the body of the patient. The guidewire is shown in FIGS. 11A-F as a guidewire 242. Typically, guidewire 242 is advanced such that it passes leaflets 12 and 14, and reaches and/or passes one or more chordae tendineae 244 (FIG. 11A). For some applications, guidewire 242 passes between two or more chordae tendineae 244. For some applications guidewire 242 is configured (e.g., shape-set) to facilitate such positioning. FIG. 11A also shows a chord-engaging tool 246 being subsequently advanced distally along guidewire 242, toward chordae tendineae 244.

Figure 11B:
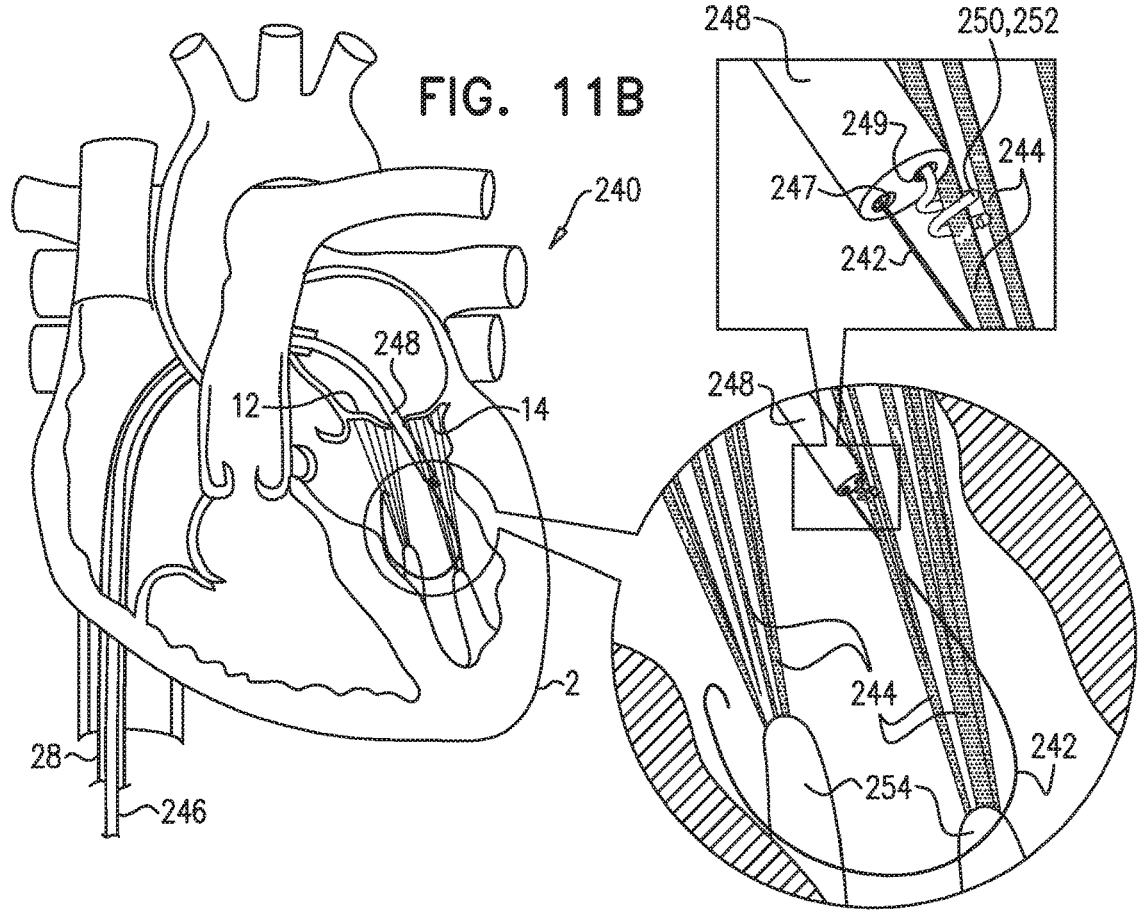

A distal portion of chord-engaging tool 246 comprises or defines a housing 248, and the chord-engaging tool is advanced such that housing 248 is disposed in a vicinity of (e.g., close to and/or touching) one or more of the chordae tendineae (FIG. 11B). Typically, tool 246 (e.g., housing 248 thereof) is shaped to define a channel 247 therethrough, through which guidewire 242 is slidable. Disposed within housing 248 is at least part of a guide member 250, which has a distal portion and a proximal portion. The distal portion of guide member 250 comprises a chord-engaging element, such as, but not limited to, a helical chord-engaging element 252, which is configured to be slidably coupled to at least one of the chordae tendineae.

FIG. 11B shows element 252 having been advanced out of an opening 249 defined by housing 248, and forming a helix outside of the housing. For some applications, when disposed within housing 248, element 252 is generally straight (e.g., is held generally straight within a lumen of the housing), and curls into the helix as it emerges from the housing. Alternatively, element 252 is also helical when disposed within housing 248. Element 252 wraps around one or more of the chordae tendineae as the element forms the helix outside of the housing. For some applications, element 252 is rotated to facilitate this wrapping. Similarly, housing 248, element 252, and guidewire 242 may be manipulated (e.g., moved back and forth) to facilitate engagement of the chordae tendineae by element 252.

FIG. 11C shows chord-engaging tool 246 (including housing 248) being subsequently moved distally such that chord-engaging element 252 slides distally along the one or more chordae tendineae that have been engaged, such that element 252 reaches (e.g., touches) a papillary muscle 254 (e.g., the papillary muscle to which the chordae tendineae engaged by element 252 is coupled).

Subsequently, tool 246 (including housing 248) is withdrawn proximally, while guide member 250 is held in place (e.g., by a counter force), such that tissue-engaging element 252 remains coupled to the chordae tendineae in close proximity to (e.g., in contact with) papillary muscle 254, and exposing the proximal portion of guide member 250, comprising a longitudinal element 251. Typically, tool 246 (including housing 248) is subsequently withdrawn into sheath 28, and further typically, is decoupled from the guide member and/or removed from the body of the patient.

FIG. 11E shows a deployment tool 260 being transcatheterally advanced into heart 2 of the subject, and being slid along guide member 250 (e.g., along longitudinal element 251 thereof). For some applications, tool 260 comprises one or more eyelets 262, slidable over longitudinal element 251. For some applications, tool 260 is advanced via an overtube 258, which may itself be advanced through sheath 28. For some applications, tool 260 is advanced via tool 246 (e.g., via a lumen therethrough), and overtube 258 in FIGS. 11E-F represents tool 246 functioning as an overtube.

Guide member 250 (e.g., longitudinal element 251 thereof) guides deployment tool 260 toward papillary muscle 254. For some applications, deployment tool 260 comprises a distal lance 264, configured to penetrate tissue of papillary muscle 254, and to stabilize tool 260 at the papillary muscle. For some such applications, lance 264 is retractable into the body of tool 260. For applications in which deployment tool comprises lance 264, the lance is typically slidable through a hole in anchor 280. Alternatively, anchor 280 may comprise lance 264, and the lance is configured to stabilize the anchor at the papillary muscle during anchoring, e.g., during rotation of the anchor.

Deployment tool 260 is configured to anchor tissue anchor 280 to papillary muscle 254. For some applications, and as shown in FIG. 11E, tissue anchor 280 is reversibly coupled to the distal end of tool 260. For some applications, the tissue anchor is housed within tool 260 and is advanced out of the tool prior to or during anchoring. For applications in which anchor 280 comprises a helical anchor, the anchor is typically anchored to the papillary muscle by being rotated by tool 260, or by a component thereof.

For some applications, system 240 is configured to facilitate anchoring of tissue anchor 280 to other ventricular muscle tissue in the vicinity of papillary muscle 254 (e.g., within 1 cm of the papillary muscle). For example, a sufficient distance between (1) a distal-most part of tool 260 at which the tool is slidably coupled to longitudinal element 251 (e.g., the distal-most eyelet 262), and (2) a distal end of anchor 280 may be provided to allow the tissue anchor to be anchored slightly away from chord-engaging element 252 (e.g., within 1 cm of the papillary muscle). Flexibility of longitudinal element 251 may alternatively or additionally facilitate such anchoring of anchor 280. Alternatively or additionally, the operating physician may stop advancing tool 260 such that a length of guide member 250 (e.g., of longitudinal element 251 thereof) between the distal-most eyelet 262 and chord-engaging element 252 is sufficient to facilitate such anchoring of anchor 280.

FIG. 11F shows guide member 250 and deployment tool 260 having been retracted proximally (e.g., into overtube 258 and/or out of the body of the patient), exposing a guidewire 282, reversibly coupled to anchor 280, and extending proximally (e.g., into overtube 258 and/or out of the body of the subject).

Chord-engaging element 252 is typically decoupled from chordae tendineae 244 by withdrawing guide member 250 slightly proximally with respect to tool 260, thereby straightening out the helix formed by element 252. For example, the helix may be progressively drawn into tool 260, or past an eyelet 262 thereof, and responsively straighten. Alternatively, chord-engaging element 252 may be decoupled from the chordae tendineae using tool 246 (e.g., housing 248 thereof), such as by re-advancing the tool distally, and withdrawing member 250, including element 252 thereof, into the tool.

For some applications, chord-engaging element 252 is decoupled from chordae tendineae 244 after anchoring of tissue anchor 280 (e.g., after tissue anchor 280 has been partially or fully advanced into papillary muscle 254). For some such applications, this is facilitated by flexibility of element 252 (e.g., that which facilitates curling and straightening thereof), e.g., by facilitating movement of element 252 through and/or around portions of anchor 280.

For some applications, chord-engaging element 252 is decoupled from chordae tendineae 244 prior to anchoring of tissue anchor 280. For example, chord-engaging element 252 may be decoupled from the chordae tendineae subsequently to lance 264 penetrating tissue and thereby stabilizing tool 260 and anchor 280 with respect to the tissue.

It is to be noted that guidewire 282 is a different guidewire to guidewire 242, described with reference to FIGS. 11A-B. As described hereinabove, for some applications, tissue anchor 280 comprises tissue anchor 50 of docking assembly 150. Similarly, guidewire 282 may comprise guidewire 40, described hereinabove, and may be reversibly coupled to anchor 280 via a docking station 56 of the docking assembly.

It is to be noted that, although guidewire 242 is shown in FIGS. 11A-E as being present in heart 2, and is shown in FIG. 11F as having been withdrawn from the heart, guidewire 242 may be withdrawn at any point in the procedure following the coupling of chord-engaging element 252 to chordae tendineae 244 (FIG. 11B).

For some applications, the step shown in FIG. 11F is generally similar to the step shown in FIG. 2. The apparatus and techniques described with reference to FIGS. 11A-F may be used in combination with the apparatus and techniques described with reference to FIGS. 1-10, e.g., to facilitate anchoring of docking assembly 150 to a papillary muscle. For some such applications, the step described with reference to FIG. 11F may precede the step shown in FIG. 3, mutatis mutandis.

For some applications of the present invention, systems 20, 220, and 240 are used to treat an atrioventricular valve other than the mitral valve, i.e., the tricuspid valve. For these applications, systems 20, 220, and 240 placed in the right ventricle instead of the left ventricle.

It is to be noted that the scope of the present invention includes the use of systems 20, 220, and 240 on other cardiac valves, such as the pulmonary valve or the aortic valve.

It is to be further noted that the scope of the present invention includes the use of systems 20, 220, and 240 on other tissue other than cardiac tissue, e.g., gastric tissue or any other suitable tissue or organ.

For some applications, system 240 and/or the techniques described with reference to FIGS. 11A-F may be used to deliver a plurality of tissue anchors 280 to the papillary muscle, and/or to deliver a plurality of tissue anchors to a plurality of papillary muscles.

Additionally, the scope of the present invention includes applications described in the following applications, which are incorporated herein by reference. In an application, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007 (which published as WO 2008/068756);

U.S. patent application Ser. No. 11/950,930 to Gross et al., entitled, "Segmented ring placement," filed on Dec. 5, 2007, which published as US Patent Application Publication 2008/0262609 (now U.S. Pat. No. 8,926,695);

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which published as 2010/0161047 (now U.S. Pat. No. 8,241,351);

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which published as 2010/0161041 (now U.S. Pat. No. 8,147,542);

U.S. patent application Ser. No. 12/437,103 to Zipory et al., entitled, "Annuloplasty ring with intra-ring anchoring," filed on May 7, 2009, which published as 2010/0286767 (now U.S. Pat. No. 8,715,342);

PCT Patent Application PCT/IL2009/000593 to Gross et al., entitled, "Annuloplasty devices and methods of delivery therefor," filed on Jun. 15, 2009, which published as WO 10/004546;

U.S. patent application Ser. No. 12/548,991 to Maisano et al., entitled, "Implantation of repair chords in the heart," filed on Aug. 27, 2009, which published as 2010/0161042 (now U.S. Pat. No. 8,808,368);

U.S. patent application Ser. No. 12/608,316 to Miller et al., entitled, "Tissue anchor for annuloplasty ring," filed on Oct. 29, 2009, which published as 2011/0106247 (now U.S. Pat. No. 8,277,502);

PCT Patent Application PCT/IL2009/001209 to Cabiri et al., entitled, "Adjustable annuloplasty devices and mechanisms therefor," filed on Dec. 22, 2009, which published as WO 10/073246;

U.S. patent application Ser. No. 12/689,635 to Zipory et al., entitled, "Over-wire rotation tool," filed on Jan. 19, 2010, which published as 2010/0280604 (now U.S. Pat. No. 8,545,553);

U.S. patent application Ser. No. 12/689,693 to Hammer et al., entitled, "Application Deployment techniques for annuloplasty ring," filed on Jan. 19, 2010, which published as 2010/0280605 (now U.S. Pat. No. 8,911,494);

U.S. patent application Ser. No. 12/706,868 to Miller et al., entitled, "Actively-engageable movement-restriction mechanism for use with an annuloplasty structure," filed on Feb. 17, 2010, which published as 2010/0211166 (now U.S. Pat. No. 8,353,956); and/or U.S. patent application Ser. No. 12/795,026 to Miller et al., entitled, "Apparatus for guide-wire based advancement of a rotation assembly," filed on Jun. 7, 2010, which published as 2011/0106245 (now U.S. Pat. No. 8,940,042).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a papillary muscle of a heart of a subject, the papillary muscle being coupled to a chorda tendinea of the heart of the subject, the method comprising:

transluminally introducing a sheath into an atrium of the heart;

advancing a guide member out of the sheath and to the chorda tendinea, the guide member having a proximal portion that includes a longitudinal element, and a distal portion that includes a helical chord-engaging element;

wrapping the chord-engaging element around the chorda tendinea; and while the chord-engaging element remains wrapped around the chorda tendinea:
sliding the chord-engaging element over the chorda tendinea toward the papillary muscle; and
subsequently, moving a tool out of the sheath and toward the papillary muscle by sliding the tool along the longitudinal element.

2. The method according to claim 1, further comprising, following the step of advancing, anchoring a tissue anchor to ventricular muscle tissue using the tool.

3. The method according to claim 2, wherein anchoring the tissue anchor comprises anchoring the tissue anchor to ventricular muscle tissue in a vicinity of the papillary muscle.

4. The method according to claim 3, wherein anchoring the tissue anchor comprises anchoring the tissue anchor to ventricular muscle tissue within 1 cm of the papillary muscle.

5. The method according to claim 3, wherein anchoring the tissue anchor comprises anchoring the tissue anchor to the papillary muscle.

6. The method according to claim 2, wherein anchoring the tissue anchor comprises anchoring a tissue anchor that is reversibly coupled to a guidewire.

7. The method according to claim 2, wherein the tool includes a lance, and the method further comprises, prior to anchoring the tissue anchor, stabilizing the tool with respect to the ventricular muscle tissue by penetrating the ventricular muscle tissue with the lance.

8. The method according to claim 7, further comprising retracting the lance into the tool.

9. The method according to claim 1, wherein the step of advancing further comprises advancing, to the heart of the subject, a housing that is slidable along the guide member.

10. The method according to claim 9, further comprising, prior to the step of advancing, advancing a guidewire to a ventricle of the heart, wherein advancing the housing comprises sliding the housing over the guidewire.

11. The method according to claim 10, wherein advancing the guidewire comprises advancing a distal portion of the guidewire between at least two chordae tendineae of the subject.

12. The method according to claim 9, further comprising, subsequent to the step of advancing, sliding the chord-engaging element distally out of the housing.

13. The method according to claim 12, further comprising, subsequent to the step of wrapping and prior to the step of moving, proximally withdrawing the housing and decoupling the housing from the guide member while maintaining the chord-engaging element wrapped around the chorda tendinea.

14. The method according to claim 12, wherein sliding the chord-engaging element distally out of the housing comprises transitioning the chord-engaging element from a generally straight state into a helical state.

* * * * *